US012714508B2

(12) United States Patent
Berman et al.

(10) Patent No.: US 12,714,508 B2
(45) Date of Patent: Aug. 25, 2026

(54) POSITIONING SYSTEM REGISTRATION USING MECHANICAL LINKAGES

(71) Applicant: Auris Health, Inc., Redwood City, CA (US)

(72) Inventors: David Burdick Berman, San Mateo, CA (US); Elif Ayvali, Redwood City, CA (US); Christopher K. Sramek, Half Moon Bay, CA (US)

(73) Assignee: Auris Health, Inc., Santa Clara, CA (US)

( * ) Notice: Subject to any disclaimer, the term of this patent is extended or adjusted under 35 U.S.C. 154(b) by 394 days.

(21) Appl. No.: 18/083,292

(22) Filed: Dec. 16, 2022

(65) Prior Publication Data

US 2023/0210604 A1 Jul. 6, 2023

Related U.S. Application Data

(60) Provisional application No. 63/295,651, filed on Dec. 31, 2021.

(51) Int. Cl.
*A61B 34/20* (2016.01)
*A61B 6/00* (2006.01)
(Continued)

(52) U.S. Cl.
CPC ................ *A61B 34/20* (2016.02); *A61B 6/12* (2013.01); *A61B 6/4441* (2013.01);
(Continued)

(58) Field of Classification Search
CPC ...... A61B 1/00149; A61B 2017/00207; A61B 2017/00725; A61B 2034/102;
(Continued)

(56) References Cited

U.S. PATENT DOCUMENTS 7,826,889 B2 11/2010 David et al.
7,971,341 B2 * 7/2011 Dukesherer ............ A61B 5/062 29/841

(Continued)

FOREIGN PATENT DOCUMENTS

WO WO-2021211650 A1 * 10/2021 ............... G06T 7/73
WO 2022217291 A1 10/2022

(Continued)

OTHER PUBLICATIONS

International Search Report for Appl. No. PCT/IB2022/062385, dated Mar. 31, 2023, 4 pages.

(Continued)

*Primary Examiner* — David J Makiya
*Assistant Examiner* — Miya Downing
(74) *Attorney, Agent, or Firm* — Paradice & Li LLP

(57) ABSTRACT

A positioning system includes a group of positioning devices including a first device comprising a first positioning source associated with a first positioning modality, the first positioning source being configured to view a first field, a second device comprising a second positioning source associated with a second positioning modality that is of a different type than the first positioning modality, the second positioning source being configured to view a second field, a third device comprising one or more first markers detectable within the first field using the first positioning modality, and a fourth device comprising one or more second markers detectable within the second field using the second positioning modality. A linking structure physically links two of the group of positioning devices to one another in a fixed, rigid relative position and orientation.

18 Claims, 12 Drawing Sheets

(51) Int. Cl.
*A61B 6/12* (2006.01)
*A61B 90/00* (2016.01)

(52) U.S. Cl.
CPC ................. *A61B 2034/2051* (2016.02); *A61B 2034/2065* (2016.02); *A61B 2090/3966* (2016.02); *A61B 2090/397* (2016.02)

(58) Field of Classification Search
CPC .... A61B 2034/2051; A61B 2034/2055; A61B 2034/2059; A61B 2034/2065; A61B 2090/0818; A61B 2090/376; A61B 2090/3762; A61B 2090/378; A61B 2090/3925; A61B 2090/3966; A61B 2090/397; A61B 2090/3983; A61B 2090/3995; A61B 34/20; A61B 34/30; A61B 5/064; A61B 5/066; A61B 6/032; A61B 6/037; A61B 6/0407; A61B 6/12; A61B 6/4441; A61B 6/487; A61B 6/547; A61B 8/0841; A61B 90/37; A61B 90/39
See application file for complete search history.

(56) References Cited

U.S. PATENT DOCUMENTS

| | | | | |
|---|---|---|---|---|
| 10,028,788 | B2 | 7/2018 | Kang | |
| 10,426,554 | B2 * | 10/2019 | Siewerdsen ............ | A61B 34/20 |
| 10,667,720 | B2 | 6/2020 | Wong et al. | |
| 2001/0031985 | A1 | 10/2001 | Gilboa et al. | |
| 2008/0204012 | A1 | 8/2008 | Krueger et al. | |
| 2010/0137707 | A1 * | 6/2010 | Hunter .................. | A61B 34/20 600/424 |
| 2012/0201421 | A1 | 8/2012 | Hartmann et al. | |
| 2012/0289821 | A1 * | 11/2012 | Graumann ........... | A61B 6/4441 378/19 |
| 2014/0049629 | A1 | 2/2014 | Siewerdsen et al. | |
| 2014/0114173 | A1 | 4/2014 | Bar-Tal et al. | |
| 2015/0335480 | A1 | 11/2015 | Alvarez et al. | |
| 2018/0256008 | A1 | 9/2018 | Nishizawa | |
| 2018/0289430 | A1 * | 10/2018 | Kahya .................. | A61B 5/6851 |
| 2021/0045822 | A1 | 2/2021 | Landey et al. | |
| 2021/0068911 | A1 | 3/2021 | Walker et al. | |
| 2021/0353362 | A1 | 11/2021 | Vaidya et al. | |

FOREIGN PATENT DOCUMENTS

| | | | |
|---|---|---|---|
| WO | 2023004303 | A1 | 1/2023 |
| WO | 2023129562 | A1 | 7/2023 |

OTHER PUBLICATIONS

Written Opinion for Appl. No. PCT/IB2022/062385, dated Mar. 31, 2023, 6 pages.
Extended European Search Report from Patent Application No. 22915306.9, dated Oct. 1, 2025, pp. 1-12.
Office Action from European Patent Application No. 22915306.9, dated Jul. 6, 2026, 6 pages.

* cited by examiner

30
ENDOSCOPE
SHAFT 40
CAMERA(S) 48
WORKING CHANNEL 44
POSITIONING MARKER(S) / SENSOR(S) 63
LIGHT(S) 49
HANDLE / BASE 31
31
40
42
10
ROBOTIC SYSTEM
CONTROL CIRCUITRY 211
COMM. INTERFACE(S) 214
POWER SUPPLY INTERFACE(S) 219
I/O COMPONTENTS 218
ARMS 12
END EFFECTORS/ IDMs 6
ACTUATOR(S)/ HARDWARE 217
10
12
24
23
24
21
17
6
25
13
20
14
27
28
50
CONTROL SYSTEM
CONTROL CIRCUITRY 251
COMM. INTERFACE(S) 254
POWER SUPPLY INTERFACE(S) 259
I/O COMPONTENTS 258
INPUT CONTROL(S) 55
DISPLAY(S) 56
50
55
51
56
58

POSITIONING SYSTEM REGISTRATION USING MECHANICAL LINKAGES

RELATED APPLICATION(S)

This application claims priority to U.S. Provisional Application No. 63/295,651, filed Dec. 31, 2021, entitled POSITIONING SYSTEM REGISTRATION USING MECHANICAL LINKAGES, the disclosure of which is hereby incorporated by reference in its entirety.

BACKGROUND

The present disclosure relates to positioning systems, including positioning systems implemented to track medical instrumentation. In particular, aspects of the present disclosure relate to the registration of different positioning systems/modalities to one another.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1:
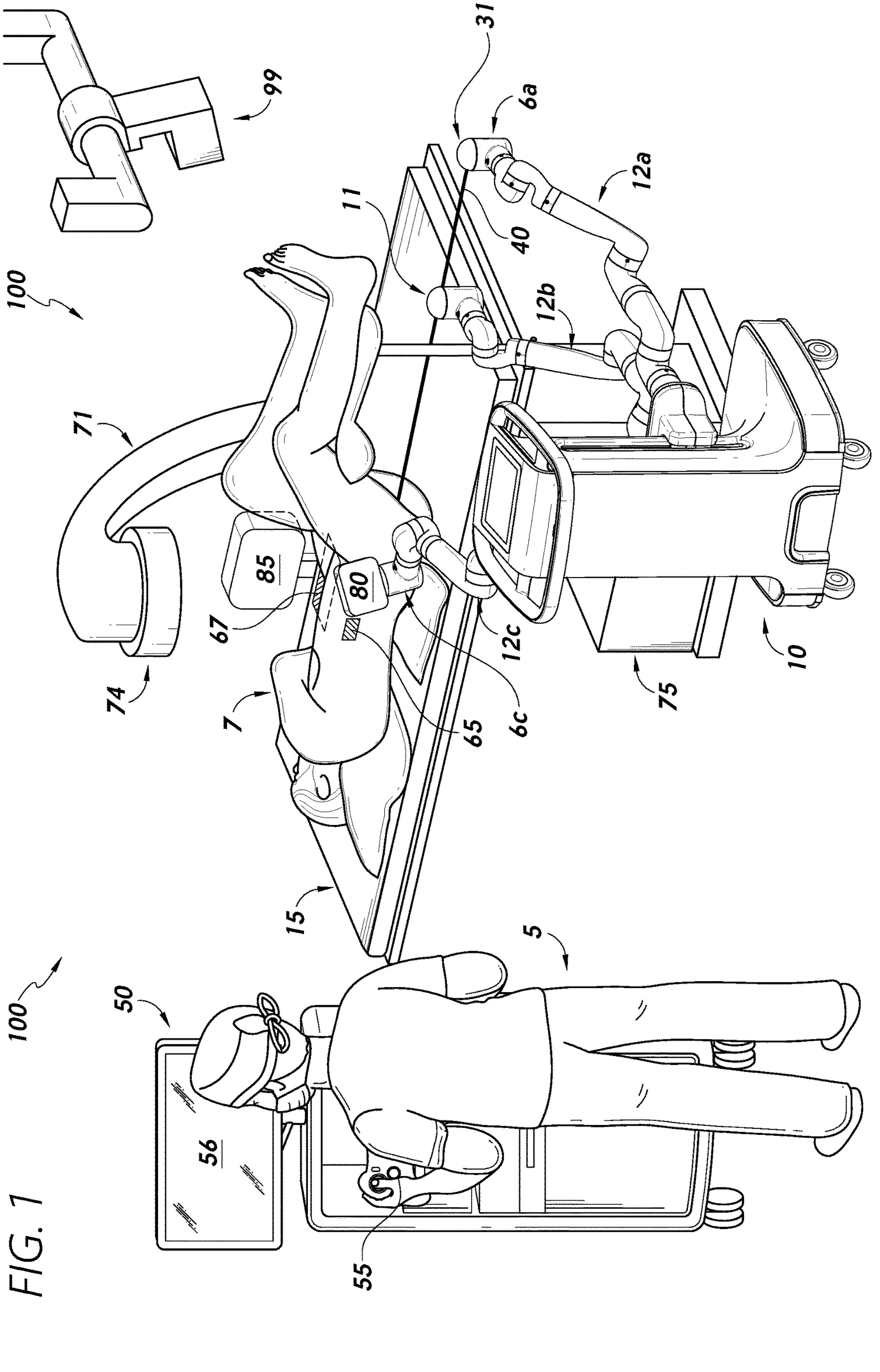
FIG. 1 illustrates an embodiment of a robotic medical system arranged for diagnostic and/or therapeutic ureteroscopy in accordance with one or more embodiments.

The headings provided herein are for convenience only and do not necessarily affect the scope or meaning of the claimed invention. Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Although certain spatially relative terms, such as "outer," "inner," "upper," "lower," "below," "above," "vertical," "horizontal," "top," "bottom," "lateral," and similar terms, are used herein to describe a spatial relationship of one device/element or anatomical structure to another device/element or anatomical structure, it is understood that these terms are used herein for ease of description to describe the positional relationship between element(s)/structures(s), such as with respect to the illustrated orientations of the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa. It should be understood that spatially relative terms, including those listed above, may be understood relative to a respective illustrated orientation of a referenced figure.

Certain reference numbers are re-used across different figures of the figure set of the present disclosure as a matter of convenience for devices, components, systems, features, and/or modules having features that may be similar in one or more respects. However, with respect to any of the embodiments disclosed herein, re-use of common reference numbers in the drawings does not necessarily indicate that such features, devices, components, or modules are identical or similar. Rather, one having ordinary skill in the art may be informed by context with respect to the degree to which usage of common reference numbers can imply similarity between referenced subject matter. Use of a particular reference number in the context of the description of a particular figure can be understood to relate to the identified device, component, aspect, feature, module, or system in that particular figure, and not necessarily to any devices, components, aspects, features, modules, or systems identified by the same reference number in another figure. Furthermore, aspects of separate figures identified with common reference numbers can be interpreted to share characteristics or to be entirely independent of one another.

In some contexts features associated with separate figures that are identified by common reference numbers are not related and/or similar with respect to at least certain aspects.

The present disclosure provides systems, devices, and methods for registering different image/positioning spaces associated with different positioning systems and/or modalities to one another. In particular, systems, devices, and methods in accordance with one or more aspects of the present disclosure can facilitate simplified multimodal registration by implementing mechanical linkages/fixation between positioning sources and/or detectable markers/sensors associated with the respective modalities.

With respect to medical instruments described in the present disclosure, the term "instrument" is used according to its broad and ordinary meaning and may refer to any type of tool, device, assembly, system, subsystem, apparatus, component, or the like. In some contexts herein, the term "device" may be used substantially interchangeably with the term "instrument."

Robotic surgical systems can be utilized to facilitate instrument navigation to areas within a patient's body. In some embodiments, robotic systems can be configured to provide an interface that allows an operator to navigate robotically-controlled instrumentation by directing the movement of the instrumentation in multiple degrees of freedom. For example, the operator may direct axial translation (i.e., insertion and/or retraction), articulation angle, and/or roll (i.e., articulation angle direction), of endoscopes, access sheaths, guidewires, working instruments (e.g., needles, baskets, lithotripsy devices, etc.). Navigation within organs, branch vessel ostia, or other relatively open three-dimensional space can be challenging due to the need to understand the three-dimensional relationship of the navigated/tracked instrument relative to the anatomical target and/or to determine in which plane the instrument will bend. This task can be difficult, in part, because navigating an instrument through a lumen of the patient from a remote patient access point to the desired site of a procedure requires manipulating the instrument without a direct line of sight of the instrument. A positioning/tracking system may be used to help locate the desired site of the procedure and visualize the navigation of the instrument to the desired site of the procedure. Positioning/tracking systems allow the user to visualize a patient's internal anatomy and the location and/or orientation of the detectable markers of the instrument within the patient's anatomy.

Positioning systems can include imaging systems/modalities, such as positron emission tomography (PET), X-ray computed tomography (CT), X-ray fluoroscopy, magnetic resonance imaging (MRI), camera-based optical systems, and ultrasonic or other sonic imaging systems. Positioning system can further include electromagnetic (EM) tracking systems (e.g., using electromagnetic field generators as described in detail herein), fiber optic tracking systems, and robotic tracking/positioning based on robotic data (e.g., robotic actuator, torque, pose data). Some imaging systems/modalities are not suitable for continuous real-time tracking of instruments, such as PET, CT, and MRI, which generally produce and combine many cross-sectional images of an object to generate a computer-processed image; such an image capture process can be relatively slow, and movement within the image field during the image capture process can produce image artifacts that make such systems unsuitable for real-time tracking of moving instruments in a body. Additionally, some imaging systems/modalities such as X-ray CT and fluoroscopy emit potentially harmful ionizing radiation, and it may be desirable to limit the duration of their use.

Electromagnetic (EM) tracking systems and fiber optic tracking systems can provide real-time instrument tracking. EM tracking generally functions by detecting/determining the position/orientation of EM sensing coil(s) (i.e., an EM marker/sensor) in a fluctuating magnetic field. The fluctuating magnetic field induces a current in the coil based on the coil's position and orientation within the field. The coil's position and orientation can thus be determined by measuring the current in the coil. In some cases, a single EM sensor/marker is able to sense its position and orientation in three-dimensional space with five degrees of freedom. That is, the EM sensor can provide data indicating orientation in every direction except around the axial symmetric axis of the coil (i.e., roll). Two EM sensors/markers held in a fixed relative position and orientation on an instrument or other marker device may be used to sense all six degrees of freedom of the instrument. In navigation systems employing EM tracking, an image of an anatomical space can be acquired, wherein the system control circuitry is configured to determine a registration between a frame of reference of the EM sensor(s)/marker(s) associated with a tracked instrument and a frame of reference of an imaging system/modality used to image the anatomical space to depict movement of the tracked instrument within the imaged anatomical space.

Although certain aspects of the present disclosure are described in detail herein in the context of bronchoscopy and ureteroscopy procedures, it should be understood that such context is provided for convenience and clarity, and instrument positioning concepts disclosed herein are applicable to any suitable medical procedures.

With respect to ureteroscopy procedures, surgeons may insert an endoscope (e.g., ureteroscope) into the urinary tract through the urethra to remove urinary stones from the bladder and ureter, such as for the purpose of removing kidney stones. In some procedures, physicians may use a percutaneous nephrolithotomy ("PCNL") technique that involves inserting a nephroscope through the skin (i.e., percutaneously) and intervening tissue to provide access to the treatment site for breaking-up and/or removing the stone(s). Relatively large kidney stones can be broken into a relatively smaller fragments to facilitate extraction thereof using certain instrumentation, such as laser lithotripsy devices. According to some procedures, a basketing device/system may be used to capture the relatively smaller stone fragment(s) and extract them from the treatment site out of the patient. Any of the instrumentation associated with such ureteroscopy procedures can be robotically-controlled and/or positionally tracked by tracking/detecting marker(s)/sensor(s) associated with the instrumentation using a positioning modality as described in detail herein.

The present disclosure provides systems, devices, and methods for registering coordinate frames of two or more positioning systems/modalities to one another. Such registration can be achieved in a simplified manner enabled by the implementation of certain mechanical/physical links/linkages between emitters and/or markers associated with different positioning modalities. In some implementations, such mechanical linkage is implemented by integrating and/or establishing a fixed relationship between markers (e.g., sensors) visible or identifiable to a plurality of different positioning modalities. For example, such integration/fixation can involve physically coupling, embedding, or overlaying markers associated with two or more different positioning modalities with/within/on one another such that the markers have a common center location and/or correspond to a common coordinate frame having a common origin. Such co-location of marker frames can eliminate the need to calculate and/or execute a transform that translates between the physical position of a marker of a first modality and the physical position of a marker of a second modality when registering the first modality to the second modality. The term "marker" is used herein according to its broad and ordinary meaning and may refer to any device or structure, or group thereof, having one or more surfaces, structures, or components that are detectable, visible, or otherwise identifiable within a positioning space (e.g., field of view) associated with a positioning modality.

In some implementations, mechanical/physical linkages between positioning modalities for the purpose of simplifying registration can involve establishing fixed relationships between emitters/sources for a plurality of positioning modalities, such as fluoroscopy, optical, robotic-pose-based, and/or electromagnetic field positioning modalities. For example, both positioning system sources/emitters can be rigidly coupled to and/or integrated with a common rigid physical structure, such as a C-arm of a fluoroscopy system. Such mechanical fixation can establish a constant positional relationship and constant registration between first and second modalities, thereby eliminating the need to calculate or execute a transform that translates between the physical position of an emitter/source of the first positioning modality and the physical position of an emitter/source of a second positioning modality when registering the first modality to the second modality.

Medical System

FIG. 1 illustrates an example medical system 100 for performing various medical procedures in accordance with aspects of the present disclosure. The medical system 100 may be used for, for example, endoscopic procedures. Robotic medical solutions can provide relatively higher precision, superior control, and/or superior hand-eye coordination with respect to certain instruments compared to strictly-manual procedures. Although the system 100 of FIG. 1 is presented in the context of a ureteroscopic procedure, it should be understood that the principles disclosed herein may be implemented in any type of endoscopic procedure.

The medical system 100 includes a robotic system 10 (e.g., mobile robotic cart) configured to engage with and/or control a medical instrument (e.g., ureteroscope) including a proximal handle 31 and a shaft 40 coupled to the handle 31 at a proximal portion thereof to perform a procedure on a patient 7. It should be understood that the instrument 40 may be any type of shaft-based medical instrument, including an endoscope (such as a ureteroscope or bronchoscope), catheter (such as a steerable or non-steerable catheter), needle, nephroscope, laparoscope, or other type of medical instrument. The instrument 40 may access the internal patient anatomy through direct access (e.g., through a natural orifice) and/or through percutaneous access via skin/tissue puncture.

The medical system 100 includes a control system 50 configured to interface with the robotic system 10, provide information regarding the procedure, and/or perform a variety of other operations. For example, the control system 50 can include one or more display(s) 56 configured to present certain information to assist the physician 5 and/or other technician(s) or individual(s). The medical system 100 can include a table 15 configured to hold the patient 7. The system 100 may further include an electromagnetic (EM) field generator, such as a robot-mounted EM field generator 80 or and EM field generator 85 mounted to the table 15 or other structure.

Although the various robotic arms 12 are shown in various positions and coupled to various tools/devices, it should be understood that such configurations are shown for convenience and illustration purposes, and such robotic arms may have different configurations over time and/or at different points during a medical procedure. Furthermore, the robotic arms 12 may be coupled to different devices/instruments than shown in FIG. 1, and in some cases or periods of time, one or more of the arms may not be utilized or coupled to a medical instrument. Instrument coupling to the robotic system 10 may be via robotic end effectors 6 associated with distal ends of the respective arms 12. The term "end effector" is used herein according to its broad and ordinary meaning and may refer to any type of robotic manipulator device, component, and/or assembly. The terms "robotic manipulator" and "robotic manipulator assembly" are used according to their broad and ordinary meanings, and may refer to a robotic end effector and/or sterile adapter or other adapter component coupled to the end effector, either collectively or individually. For example, "robotic manipulator" or "robotic manipulator assembly" may refer to an instrument device manipulator (IDM) including one or more drive outputs, whether embodied in a robotic end effector, adapter, and/or other component(s).

In some embodiments, the physician 5 can interact with the control system 50 and/or the robotic system 10 to cause/control the robotic system 10 to advance and navigate the medical instrument shaft 40 (e.g., a scope) through the patient anatomy to the target site and/or perform certain operations using the relevant instrumentation. The control system 50 can provide information via the display(s) 56 that is associated with the medical instrument 40, such as real-time endoscopic images captured therewith, and/or other instruments of the system 100, to assist the physician 5 in navigating/controlling such instrumentation. The control system 50 may provide imaging/positional information to the physician 5 that is based on certain positioning modalities, such as fluoroscopy, ultrasound, optical/camera imaging, EM field positioning, or other modality, as described in detail herein.

The various scope/shaft-type instruments disclosed herein, such as the shaft 40 of the system 100, can be configured to navigate within the human anatomy, such as within a natural orifice or lumen of the human anatomy. The terms "scope" and "endoscope" are used herein according to their broad and ordinary meanings, and may refer to any type of elongate (e.g., shaft-type) medical instrument having image generating, viewing, and/or capturing functionality and being configured to be introduced into any type of organ, cavity, lumen, chamber, or space of a body. A scope can include, for example, a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), colonoscope (e.g., for accessing the colon and/or rectum), borescope, and so on. Scopes/endoscopes, in some instances, may comprise an at least partially rigid and/or flexible tube, and may be dimensioned to be passed within an outer sheath, catheter, introducer, or other lumen-type device, or may be used without such devices. Endoscopes and other instruments described herein can have associated with distal ends or other portions thereof certain markers/sensors configured to be visible/detectable in a field/space associated with one or more positioning (e.g., imaging) systems/modalities.

The system 100 is illustrated as including a fluoroscopy system 70, which includes an X-ray generator 75 and an image detector 74 (referred to as an "image intensifier" in some contexts; either component 74, 75 may be referred to as a "source" herein), which may both be mounted on a moveable C-arm 71. The control system 50 or other system/device may be used to store and/or manipulate images generated using the fluoroscopy system 70. In some embodiments, the bed 15 is radiolucent, such that radiation from the generator 75 may pass through the bed 15 and the target area of the patient's anatomy, wherein the patient 7 is positioned between the ends of the C-arm 71. The structure/arm 71 of the fluoroscopy system 70 may be rotatable or fixed. The fluoroscopy system 70 may be implemented to allow live images to be viewed to facilitate image-guided surgery. The structure/arm 71 can be selectively moveable to permit various images of the patient 7 and/or surgical field to be taken by the fluoroscopy panel source 74.

In the example urology configuration shown in FIG. 1, the robotic arm 12*c* is shown holding the field generator 80. As the electric field generated by the electric field generator 80 can be distorted by the presence of metal or other conductive components therein, it may be desirable to position the arm 12*c* in a manner such that other components of the system do not interfere substantially with the electric field. For example, it may be desirable to position the field generator 80 at least 8" or more away from the support arm 71 associated with the fluoroscopy system. In some embodiments, the system 100 includes an EM field generator 85 mounted to the table 15 or other structure (e.g., stand-alone structure).

The system 100 (as with other systems disclosed herein) can include an optical imaging source 99, such as a camera device (e.g., stereoscopic camera assembly). The optical imaging source 99 may be configured/used to view a field in the surgical environment to identify certain marker(s) disposed in the visual field. For example, in some embodiments, the imaging source 99 may emit infrared (IR) or other-frequency electromagnetic radiation and/or detect reflection of such radiation to identify markers that include surfaces that reflect such radiation. Such optical deflection can indicate position and/or orientation of the marker(s) associated with the particular optical modality. The system 100 can have certain markers/fiducials 65, 67, which may be detectable/positionable in one or more reference/coordinate frames/spaces associated with respective positioning modalities.

Figure 2:
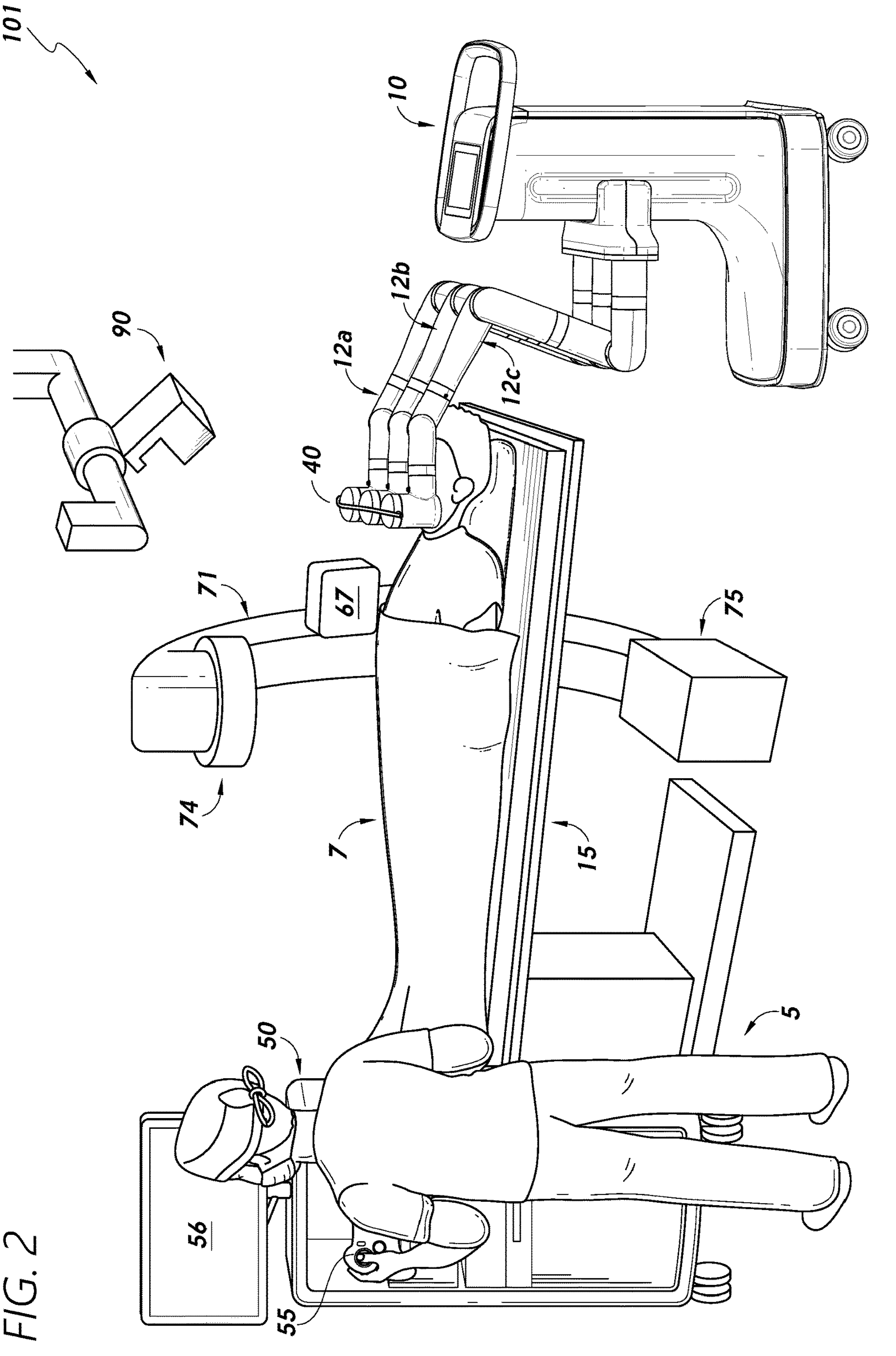
FIG. 2 illustrates a robotic system arranged for diagnostic and/or therapeutic bronchoscopy in accordance with one or more embodiments.

FIG. 2 illustrates a cart-based robotic system 101 arranged for diagnostic and/or therapeutic bronchoscopy in accordance with one or more embodiments. During a bronchoscopy, the arm(s) 12 of the robotic system 10 may be configured to drive a medical instrument shaft 40, such as a steerable endoscope, which may be a procedure-specific bronchoscope for bronchoscopy, through a natural orifice access point (e.g., the mouth of the patient 7 positioned on a table 15 in the present example) to deliver diagnostic and/or therapeutic tools. As shown, the robotic system 10 (e.g., cart) may be positioned proximate to the patient's upper torso in order to provide access to the access point. The arrangement in FIG. 2 may also be utilized when performing a gastro-intestinal (GI) procedure with a gastroscope.

As with the system 100 of FIG. 1, the instrument/scope 40 may access the target anatomy through an access sheath. For surgical bronchoscopy, the endoscope 40 may be directed down the patient's trachea and lungs after insertion using precise commands from the robotic system 10 until reaching the target operative site. For example, the endoscope 52 may be directed to deliver a biopsy needle to a target, such as, for example, a lesion or nodule within the lungs of a patient. The system 101 can include an optical-/camera-based positioning/imaging source 90.

Figure 3:
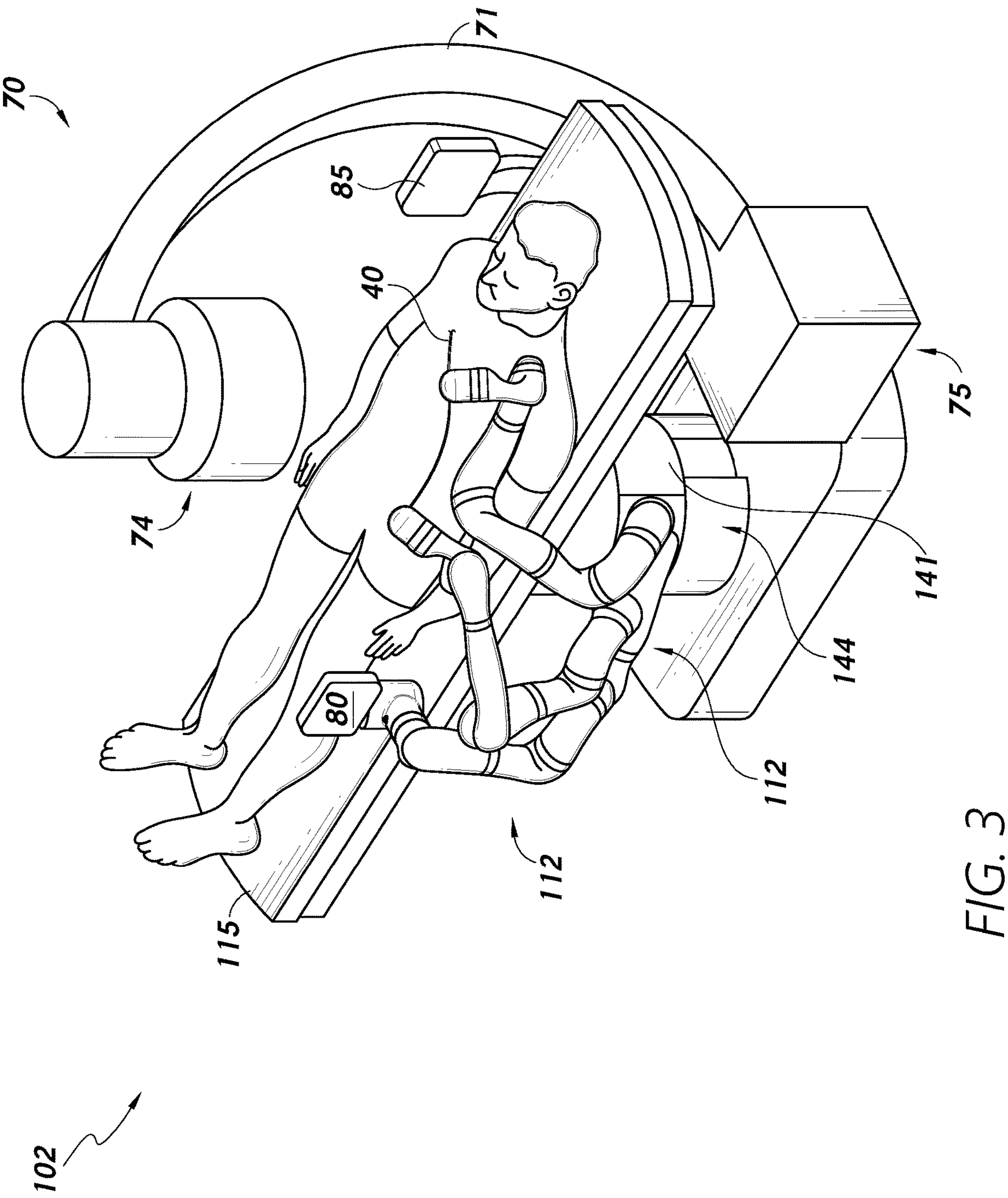
FIG. 3 illustrates a table-based robotic system in accordance with one or more embodiments.

FIG. 3 illustrates a table-based robotic system 102 in accordance with one or more embodiments of the present disclosure. The system 102 incorporates robotic components integrated with a table/platform 115, thereby allowing for a reduced amount of capital equipment within the operating room compared to some cart-based robotic systems. Table-integrated robotic systems like the system 102 can allow greater access to patients in some instances. Much like in the cart-based systems 101, 102, the instrument device manipulator assemblies associated with the robotic arms 112 of the system 102 may generally comprise instruments and/or instrument feeders that are designed to manipulate an elongated medical instrument/shaft, such as a catheter 40 or the like.

As shown, the robotic-enabled table system 104 can include a column 144 coupled to one or more carriages 141 (e.g., ring-shaped movable structures), from which the one or more robotic arms 112 may emanate. The carriage(s) 141 may translate along a vertical column interface that runs at least a portion of the length of the column 144 to provide different vantage points from which the robotic arms 112 may be positioned. The carriage(s) 141 may rotate around the column 144 in some embodiments to allow the robotic arms 112 to have access to multiples sides of the table 104. Rotation and/or translation of the carriage(s) 141 can allow the system 102 to align the medical instruments, such as endoscopes and catheters, into different access points on the patient.

In any of the systems of FIGS. 1-3, tracking of the position of instrumentation robotically advanced within the patient can be facilitated by the use of a plurality of positioning modalities, including, for example, fluoroscopy, EM field sensing, optical imaging, robotic pose estimation, ultrasound, and the like. Registration of the plurality of modalities to one another, as described in detail herein, can allow for determined positions in one modality to be tracked and/or superimposed on an image field associated with another modality. Markers may be placed on, or otherwise integrated with, the tracked instruments to allow for such markers/instruments to be detected and localized in the respective positioning/image spaces of the relevant positioning modalities. As for the tracking of target anatomy within the patient, an endoscope or other instrument may be used to deliver/indicate a fiducial to "mark" the location of the target anatomy.

With reference to FIGS. 1-3 and FIG. 4, which shows example embodiments components of subsystems of any of FIGS. 1-3, the control system 50 can be configured to provide various functionality to assist in performing a medical procedure. The control system 50 can communicate with the robotic system 10 via a wireless or wired connection (e.g., to control the robotic system 10). In some embodiments, the control system 50 can communicate with the robotic system 10 to receive position data therefrom relating to the position of the distal end of the scope 40 or other instrumentation. Such positioning data may be derived using one or more markers (e.g., electromagnetic sensors, radiopaque markers, etc.) associated with the respective instrumentation and/or based at least in part on robotic system data (e.g., arm position/pose data, known parameters or dimensions of the various system components, etc.). In some embodiments, the control system 50 can communicate with the EM field generator 80/85 to control generation of an EM field in an area around the patient 7 and/or around the tracked instrumentation.

Figure 4:
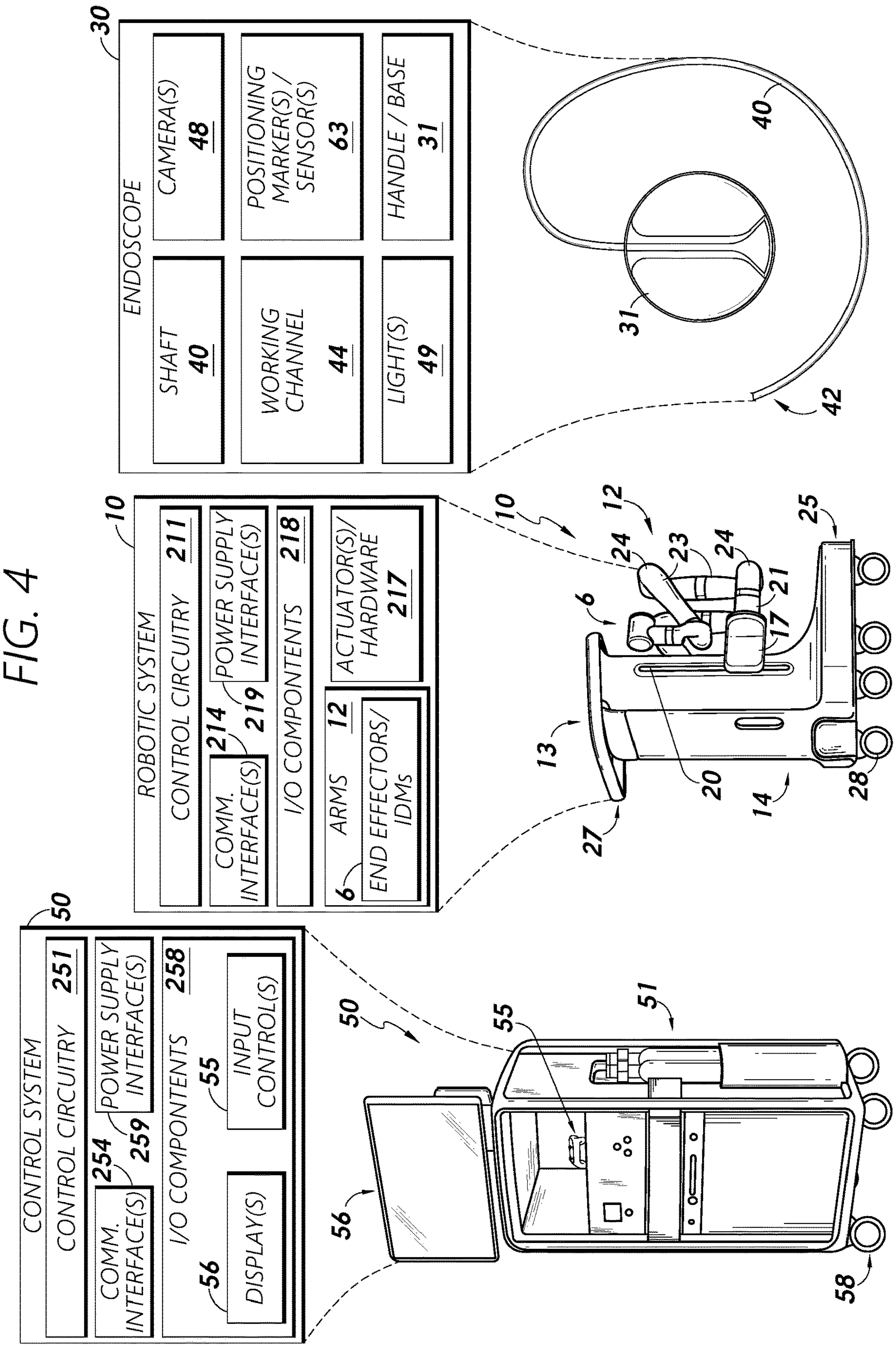
FIG. 4 illustrates medical system components that may be implemented in any of the medical systems of FIGS. 1-3 in accordance with one or more embodiments.

FIG. 4 further shows an example embodiment of the robotic systems 10 of any of FIGS. 1-3. The robotic system 10 can include one or more robotic arms 12, each of which can include multiple arm segments 23 coupled to joints 24, which can provide multiple degrees of movement/freedom. When the robotic system 10 is properly positioned, the scope 40 can be inserted into the patient 7 robotically using the robotic arms 12, manually by the physician 5, or a combination thereof. One of the arms 112 may have associated therewith an instrument coupling/manipulator 31 that is configured to facilitate advancement and operation of the scope 40.

The robotic system 10 can be physically and/or communicatively coupled to any component of the medical system, such as to the control system 50, the table 15, the EM field generator 80/85, the scope 40, the fluoroscopy system 70, and/or any type of percutaneous-access instrument (e.g., needle, catheter, nephroscope, etc.). The robotic system 10 may be configured to receive control signals from the control system 50 to perform certain operations, such as to position one or more of the robotic arms 12, manipulate the scope 40, and so on. In response, the robotic system 10 can control, using certain control circuitry 211, actuators 217, and/or other components of the robotic system 10 to perform the operations. For example, the control circuitry 211 may control various motors/actuators associated with the various joints of the robotic arms 12 and/or the arm support 17. In some embodiments, the robotic system 10 and/or control system 50 is/are configured to receive images and/or image data from the scope 40 representing internal anatomy of the patient 7 and/or portions of the access sheath or other device components.

The robotic system 10 generally includes an elongated support structure 14 (also referred to as a "column"), a robotic system base 25, and a console 13 at the top of the column 14. The column 14 may include one or more arm supports 17 (also referred to as a "carriage") for supporting the deployment of the one or more robotic arms 12 (three shown in FIG. 1). The arm support 17 may be configured to vertically translate along the column 14. In some embodiments, the arm support 17 can be connected to the column 14 through slots 20 that are positioned on opposite sides of the column 14 to guide the vertical translation of the arm support 17. The slot 20 contains a vertical translation interface to position and hold the arm support 17 at various vertical heights relative to the robotic system base 25. The base 25 balances the weight of the column 14, arm support 17, and arms 12 over the floor.

The robotic arms 12 may generally comprise robotic arm bases 21 and end effectors 6, separated by a series of linking arm segments 23 that are connected by a series of joints 24, each joint comprising one or more independent actuators 217. Each actuator may comprise an independently-controllable motor. Each independently-controllable joint 24 can provide or represent an independent degree of freedom available to the robotic arm. In some embodiments, each of the arms 12 has seven joints, and thus provides seven degrees of freedom, including "redundant" degrees of freedom. Redundant degrees of freedom allow the robotic arms 12 to position their respective end effectors 6 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions. Positioned at the upper end of column 14, the console 13 can provide both a user interface for receiving user input and a display screen 56 (or a dual-purpose device such as, for example, a touchscreen) to provide the physician/user with both pre-operative and intra-operative data. The robotic cart 10 can further include a handle 27, as well as one or more wheels 28.

The end effector 6 of each of the robotic arms 12 may comprise, or be configured to have coupled thereto, an instrument device manipulator (IDM; e.g., scope handle 31), which may be attached using a sterile adapter component in some instances. The combination of the end effector 6 and associated IDM, as well as any intervening mechanics or couplings (e.g., sterile adapter), can be referred to as a manipulator assembly. An IDM can provide power and control interfaces. For example, the interfaces can include connectors to transfer pneumatic pressure, electrical power, electrical signals, and/or optical signals from the robotic arm 12 to the IDM. The IDMs may be configured to manipulate medical instruments (e.g., surgical tools/instruments), such as the scope 40, using techniques including, for example, direct drives, harmonic drives, geared drives, belts and pulleys, magnetic drives, and the like.

As referenced above, the system 100 can include certain control circuitry configured to perform certain of the functionality described herein, including the control circuitry 211 of the robotic system 10 and the control circuitry 251 of the control system 50. That is, the control circuitry of the systems 100, 101, 102 may be part of the robotic system 10, the control system 50, or some combination thereof. Therefore, any reference herein to control circuitry may refer to circuitry embodied in a robotic system, a control system, or any other component of a medical system, such as the medical systems 100, 101, and 102 shown in FIGS. 1-3, respectively. The term "control circuitry" is used herein according to its broad and ordinary meaning, and may refer to any collection of processors, processing circuitry, processing modules/units, chips, dies (e.g., semiconductor dies including one or more active and/or passive devices and/or connectivity circuitry), microprocessors, micro-controllers, digital signal processors, microcomputers, central processing units, field-programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry referenced herein may further include one or more circuit substrates (e.g., printed circuit boards), conductive traces and vias, and/or mounting pads, connectors, and/or components. Control circuitry referenced herein may further comprise one or more storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry.

The control circuitry 211, 251 may comprise computer-readable media storing, and/or configured to store, hard-coded and/or operational instructions corresponding to at least some of the steps and/or functions illustrated in one or more of the present figures and/or described herein. Such computer-readable media can be included in an article of manufacture in some instances. The control circuitry 211/251 may be entirely locally maintained/disposed or may be remotely located at least in part (e.g., communicatively coupled indirectly via a local area network and/or a wide area network). Any of the control circuitry 211, 251 may be configured to perform any aspect(s) of the various processes disclosed herein.

With further reference to FIG. 4, the control system 50 can include various I/O components 258 configured to assist the physician 5 or others in performing a medical procedure. For example, the input/output (I/O) components 258 can be configured to allow for user input to control/navigate the scope 40 and/or basketing system within the patient 7. In some embodiments, for example, the physician 5 can provide input to the control system 50 and/or robotic system 10, wherein in response to such input, control signals can be sent to the robotic system 10 to manipulate the scope 40 and/or other robotically-controlled instrumentation.

The control system 50 and/or robotic system 10 can include certain user controls (e.g., controls 55), which may comprise any type of user input (and/or output) devices or device interfaces, such as one or more buttons, keys, joysticks, handheld controllers (e.g., video-game-type controllers), computer mice, trackpads, trackballs, control pads, and/or sensors (e.g., motion sensors or cameras) that capture hand gestures and finger gestures, touchscreens, and/or interfaces/connectors therefore. Such user controls are communicatively and/or physically coupled to respective control circuitry. The control system can include a structural tower 51, as well as one or more wheels 58 that support the tower 51. The control system 50 can further include certain communication interface(s) 254 and/or power supply interface(s) 259.

In some embodiments, the endoscope assembly 30 includes a handle or base 31 coupled to an endoscope shaft 40 (referred to simply as an "endoscope," or "scope" in certain contexts herein). For example, the endoscope 40 can include an elongate shaft including one or more lights 49 and one or more cameras or other imaging devices 48. The scope 40 can further include one or more working channels 44, which may run a length of the scope 40.

The scope assembly 30 can further comprise one or more positioning markers and/or sensors 63, which may be configured to generate signals indicating a position of the marker(s)/sensor(s) 63 within an electromagnetic field. Such markers 63 may comprise, for example, one or more conductive coils (or other embodiment of an antenna), which may be disposed at a known, fixed orientation relative to one another to allow for the determination of multiple degrees of freedom with respect to position determination. The marker(s) 63 can be configured to generate and/or send sensor position data to another device and/or produce a detectable distortion or signature in an electromagnetic field. The sensor/marker position data can indicate a position and/or orientation of the medical instrument 40 (e.g., the distal end 42 thereof) and/or can be used to determine/infer a position/orientation of the medical instrument.

The scope 40 can be articulable, such as with respect to at least a distal portion 42 of the scope 40, so that the scope 40 can be steered within the human anatomy. In some embodiments, the scope 40 is configured to be articulated with, for example, six degrees of freedom, including XYZ coordinate movement, as well as pitch, yaw, and roll. Certain position sensor(s) (e.g., electromagnetic sensors) of the scope 40, where implemented, may likewise have similar degrees of freedom with respect to the positional information they generate/provide.

For robotic implementations, robotic arms of a robotic system can be configured/configurable to manipulate the scope 40. For example, an instrument device manipulator (e.g., scope handle) can be coupled to an end effector of a robot arm and can manipulate the scope 40 using elongate movement members. The elongate movement members may include one or more pull wires (e.g., pull or push wires), cables, fibers, and/or flexible shafts. For example, the robotic end effector may be configured to actuate multiple pull wires (not shown) coupled to the scope 40 to deflect the tip 42 of the scope 40.

In various embodiments, the anatomical space in which the scope 40 or other instrument may be localized (i.e., where position of the scope/instrument is determined/estimated) is a three-dimensional portion of a patient's vasculature, tracheobronchial airways, urinary tract, gastrointestinal tract, or any organ or space accessed via such lumens. Various positioning/imaging modalities may be implemented to provide images/representations of the anatomical space. Suitable imaging subsystems include, for example, X-ray, fluoroscopy, CT, PET, PET-CT, CT angiography, Cone-Beam CT, 3DRA, single-photon emission computed tomography (SPECT), MRI, Optical Coherence Tomography (OCT), and ultrasound. One or both of pre-procedural and intra-procedural images may be acquired. In some embodiments, the pre-procedural and/or intra-procedural images are acquired using a C-arm fluoroscope. In connection with some embodiments, particular positioning and imaging systems/modalities are described; it should be understood that such description may relate to any type of positioning system/modality.

Figure 5:
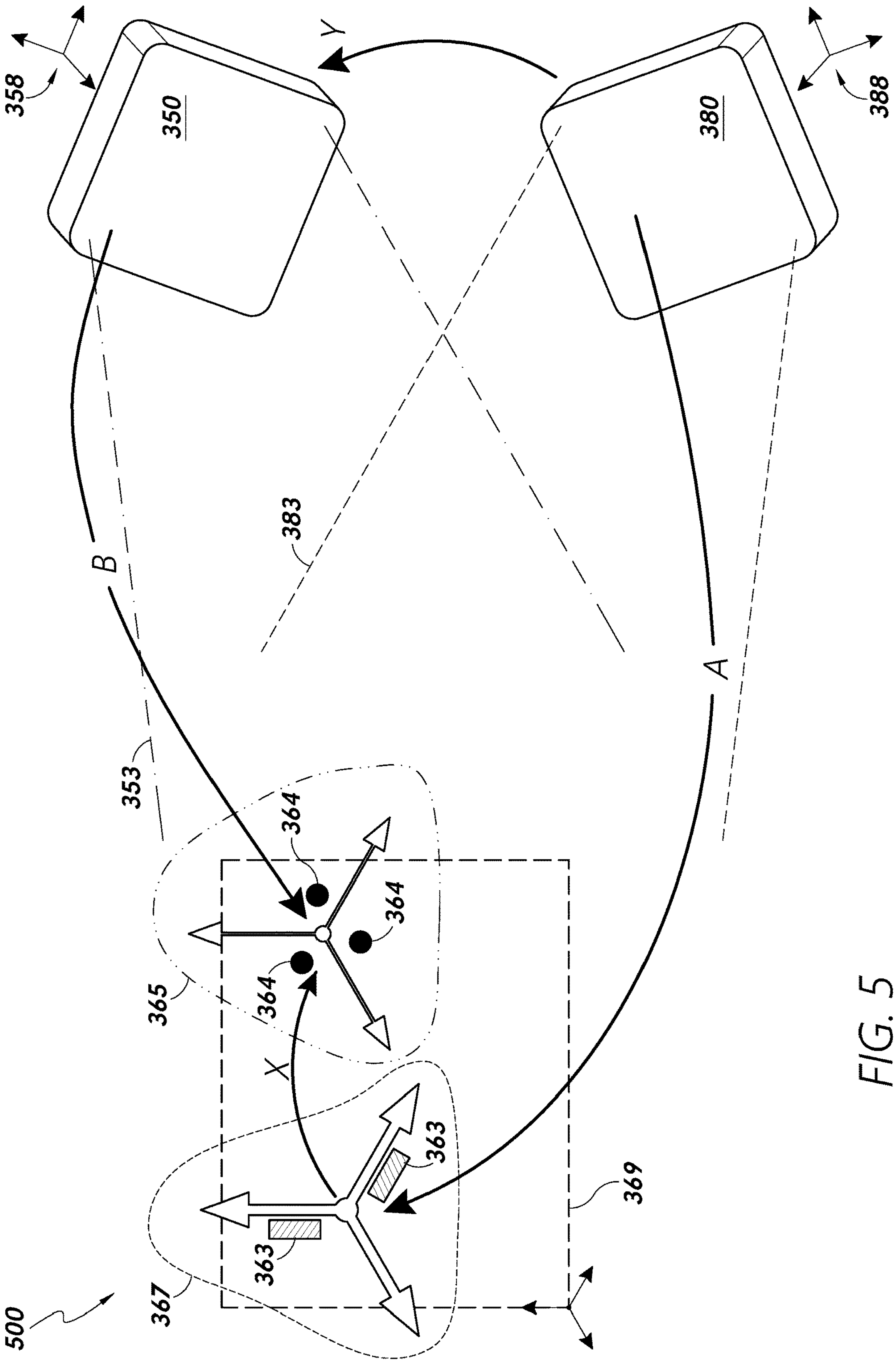
FIG. 5 illustrates an arrangement of a plurality of positioning systems in accordance with one or more embodiments.

FIG. 5 illustrates an arrangement of a plurality of positioning systems/modalities in accordance with one or more embodiments. In particular, the system of FIG. 5 includes a first positioning system/modality 350 and a second positioning system/modality 380. Each of the positioning systems 350, 380 includes a generator/source device, such as a camera, electromagnetic field generator, radiofrequency radiation generator, ionizing radiation generator (e.g., x-ray/fluoroscopy), or the like. Each of the modalities/systems is configured to detect/identify a respective marker or set of markers 365, 367 to determine the position thereof. It should be understood that the modalities/systems shown in FIG. 5 can be any type of imaging or positioning system. Therefore, although certain aspects of the system 500 are described below in the context of particular modalities/systems, such example modalities/systems are described for convenience, and it should be understood that the description thereof relates to other types of modalities/systems as well.

In an example system, the first modality 350 may be an imaging modality, such as an optical camera-based system, wherein the source 350 comprises one or more cameras associated with a visual field 353. Placement in the visual field of certain markers may allow for positioning/localization of the markers in the visual field by processing of image(s) captured by the camera(s). In some implementations, the imaging source 350 comprises a plurality of cameras set at relative angular offsets with respect to one another in a manner as to provide images that include information from which three-dimensional (3D) positioning can be derived.

In some embodiments, the positioning system 350 is a fluoroscopy system or other imaging system. For example, as shown in FIGS. 1-3, the fluoroscopy system can include a C-arm or other structural support component(s). In some implementations, it may be necessary or desirable to physically move and/or reorient the imaging source 350 to obtain a plurality of images at different angles that allow for 3D positioning to be derived from the generated images.

As another example, the second modality/system 380 may be an electromagnetic (EM) field generator system, as described in detail herein. The field generator 380 may comprise one or more antennas configured to emanate an electromagnetic field 383 in a defined area, wherein certain sensors 363, such as conductive coils or the like, placed within the electromagnetic field 383 are detectable due to the current induced therein resulting from the electromagnetic field.

The EM positioning system 380 can be used to track a medical instrument, such as an endoscope. For example, the sensors/markers 363 may be integrated with a distal end of the endoscope to allow for localization of the scope using the EM system 380. As used herein, a positioning system may also be referred to as a tracking system, a shape tracking system, or a localization subsystem. The term "localization" is used herein according to its broad and ordinary meaning and may refer to systems and methods for determining and/or monitoring the position (i.e., location and/or orientation) of objects, such as medical instruments or tools in a reference coordinate system. The term "localized" is likewise used herein according to its broad and ordinary meaning and may refer to detected/sensed markers, the position and/or orientation of which has been identified with respect to a particular coordinate system/frame. The reference coordinate system may be, for example, an image of the patient or a part of the patient anatomy.

Control circuitry of the relevant system may be utilized to detect the one or more markers/sensors 367 and/or receive data from the one or more markers/sensors 367. In some embodiments, the positioning system 380 is a fiber optic tracking system or other positioning/localization system. Some positioning systems/components are referred to herein as EM sensor systems/components to avoid listing numerous sensors for each embodiment, but it should be emphasized that any positioning systems, including fiber optic sensor systems, may be used.

Each of the positioning systems/sources 350, 380 may define a separate reference frame to which markers detectable within the view field of the respective system may be localized. The present disclosure relates to the relating (i.e., "registering") of a coordinate system/frame of one positioning system (e.g., an EM positioning system) to another a coordinate system/frame of another positioning system (e.g., a fluoroscopy system). Control circuitry associated with the system(s) may employ various registration techniques to register the different modalities to one another.

With respect to EM-to-fluoroscopy (or other positioning system) registration, when the EM sensor marker(s) 367 are integrated into a tracked instrument (e.g., scope) are localized and registered to an image space (e.g., fluoroscopy image(s)) of the anatomy such that the position of the instrument is determined relative to the anatomical image space, a positionally-accurate representation of the instrument can be provided in the coordinate frame of the anatomical image(s). As the instrument moves through the patient, the tracking information of the marker(s) can be used to update the position of the instrument relative to the anatomy/image such that the representation of the instrument can be displayed moving in real-time in an anatomical image. Additionally, with the instrument and the anatomical images provided in the same frame of reference, target anatomy may be identified in multiple images (e.g., fluoroscopy views) to localize the target's position in three dimensional (3-D) space relative to the instrument.

In some embodiments, a tracked instrument or calibration structure is equipped with two five-degrees-of-freedom (DOF) EM sensors/markers, which can collectively provide six degrees of freedom, including position (x, y, z), heading (pitch and yaw), and roll orientation information, when positioned at certain known relative position/orientation. For example, two 5-DOF coils can be combined into a rigid assembly in a medical instrument or calibration structure with known sensor locations, wherein the two coils are configured to have different orientations of their symmetric axes.

As referenced above, registration is a process that involves relating the reference frame of a first positioning system/modality (e.g., EM positioning system) to aa reference frame of a second positioning system/modality (e.g., fluoroscopy, optical/camera, or other imaging system). If the positions of two or more objects are known in the same reference frame (i.e., are mapped to the same coordinate system), then the actual positions of each object relative to each other may be ascertained. Thus, with this information, a user can drive or manipulate one of the objects relative to the other object.

In various embodiments, an EM field reference frame (e.g., frame 388) is registered to a fluoroscopy reference frame (e.g., frame 358). For example, in some embodiments, the EM reference frame is measured in relation to the fluoroscopy system reference frame. For example, in some embodiments, a sensing probe/structure 369 is used, which has EM sensor(s) and a radiopaque marker visible under fluoroscopy located in the same physical location on the probe and/or in a fixed position relative to the EM sensor(s). The sensing probe/structure can be placed into the field of view of the EM field generator and the fluoroscopy source. The two-dimensional position of the probe/structure can be designated by the user in the fluoroscopy field of view in images obtained at two different C-arm roll angles. In some implementations, the position of the probe is designated by the user in three or more different locations. These measurements can be used to sync the sensor location measurements with the selected fluoroscopy locations. In this way, the EM coordinate system can be registered to the fluoroscopy coordinate system.

FIG. 5 shows a first marker 365 detectable in the field of view 353 of the first positioning system 350 (e.g., fluoroscopy) and a second marker 367 detectable in the field of view 383 of the second positioning system 380. In some implementations, the marker(s) associated with either or both of the positioning systems/modalities may be mechanically fixed to a fixture 369, such as a fixture/probe coupled to a robotic arm or other structure in the surgical environment. In situations in which the markers 365, 367 are not mechanically fixed to a common structure, the physical transform 'X' between the markers generally affects the registration of the reference frames 358, 388.

In order to register the different positioning modalities/systems to one another, it may be necessary to perform one or more transforms representing the difference in physical position and/or orientation of the sources 350, 380 and/or respective markers 364, 363. For example, where one of the modalities 350, 380 provides certain images of the surgical field that provides a visual aid for the operator, it may be necessary or desirable to determine where in such images/image space detected markers associated with the other of the modalities 350, 380 are present as a means of merging the information provided by both modalities in a common positioning reference frame. Registering multiple positioning modalities, such as electromagnetic sensing, fluoroscopy, ultrasound, or the like, can allow for the bringing-together of the positioning spaces of the respective modalities, to thereby allow for the extraction of information from different modalities/systems and the fusing of such systems together for use during navigation and/or other processes.

Generally, registration of the modalities 350, 380 to one another may be based on the physical positional/orientational transform between the sources 'Y' and/or the markers 'X,' as shown in the illustrated diagram. Specifically, the registration of the modalities 380, 350 may be based at least in part on the following equation/relationship:

$$AX=YB \quad (1)$$

wherein 'A' represents the physical transform/relationship between the source 380 and the sensor(s)/marker(s) 367 of the positioning system 380, and 'B' represents the physical transform/relationship between the source 350 and the sensor(s)/marker(s) 365 of the positioning system 350. Therefore, in order to determine the registration between the modalities 350, 380, it may be necessary to determine at least one of the physical transforms 'X,' 'Y' in order to place a determined position of a marker in the coordinate space of the other positioning system/modality. The calculation of such transforms can be undesirably complicated, time-consuming, and/or resource-intensive. Embodiments of the present disclosure provide simplified registration solutions, wherein the need to calculate either or both of the physical transforms 'X,' 'Y' is obviated through the use of mechanical linkages between the sources 350, 380 and/or markers 365, 367.

The term "registration" is used herein according to its broad and ordinary meaning, and may refer to means, processes, and/or mechanisms for finding the coordinate transform between two separate coordinate/reference frames. Likewise, the term "calibration" is used herein according to its broad and ordinary meaning, and may refer to means, processes, and/or mechanisms for correcting and/or compensating for error in the definition of a coordinate/reference frame.

Extrinsic calibration in accordance with embodiments of the present disclosure can involve calibrating the frame of an imaging sensor with respect to another reference/coordinate frame. Such calibration may be done by registering the frames to one another. Therefore, registration and extrinsic calibration can be considered part of the same process for imaging sources (e.g., camera-based, optical-base, fluoroscopy-based systems). "Registration" may be used herein as a term that is more general than extrinsic calibration, and describes the determination of transforms between any two coordinate frames. With respect to various embodiments and figures described herein, "registration" may represent the transform 'Y,' described in detail herein. In some contexts, performing a registration process can be referred to as extrinsic calibration.

In addition to the extrinsic calibration referenced above, it should be understood that where one of the positioning systems (e.g., the system 350) is an imaging modality, such as an optical imaging system, intrinsic calibration may further be necessary to compensate for distortion and any mismatches with respect to, for example, focal length and/or other parameter(s) between manufacturing specifications and actual conditions (e.g., actual focal length). Intrinsic calibration of an imaging modality can involve the calibration of pixel coordinates and camera coordinates in the image frame. Embodiments of the present disclosure provide solutions for simplifying or obviating aspects of extrinsic calibration, e.g., relating to determination of relative position/pose between sources and/or markers of sensing modalities, using mechanical linkages. Any of the markers 365, 367 and/or positioning system sources 350, 380 can be considered positioning devices. That is, positioning devices of the embodiments of the present disclosure can be positioning markers or sources, and/or structure associated therewith, either alone or in combination.

Registration Solutions Based on Mechanical Linkages

According to aspects of the present disclosure, registration between multiple positioning modalities can be facilitated by implementing mechanical linkages between different positioning sources and/or markers. For example, by implementing a fixed/known physical relationship between sources of two different modalities/systems and/or markers of two different modalities/systems, either or both of the transforms 'X' and 'Y,' as shown in FIG. 5, may be determined without further calculation, thereby simplifying the registration equation AX=YB. That is, with respect to the equation AX=YB, by implementing known/fixed physical relationships between the sources 350, 380 and/or markers 363, 364, either or both of the parameters 'X,' 'Y' may be set to a known constant (e.g., value, vector, matrix, etc.). For example, the value of 'X' can be equal to a value of 1 (i.e., identity transform), and therefore ignored for the purposes of calculation, in implementations in which sources and/or markers are co-located in a common physical position and/or in a position having a common center and/or coordinate frame. Therefore, embodiments of the present disclosure can allow for substitution of algorithmic registration solutions with mechanical known/direct computation.

Localization Marker Consolidation

As described above, certain markers or sensors, referred to in some contexts herein as "fiducials," may be used for localization within a coordinate frame associated with a particular positioning modality. For example, such markers may be visible/identifiable within a field of view (e.g., electromagnetic field, camera image field, fluoroscopy X-ray field) due to the presence of certain characteristics/features that are visible with respect to the respective modality. Markers that are detectable/identifiable with a sufficient degree of accuracy within a particular positioning space can be useful for completing certain procedures and/or to evaluate accuracy of one or more modalities. Such markers can be used to create a reference point (e.g., with respect to position and/or orientation) in a single image space, such as computed tomography (CT), optical camera space, ultrasound, or the like. Embodiments of the present disclosure provide for multi-modal markers/fiducials that can be used to establish reference point(s) in more than one image space, such as in CT/fluoroscopy space and EM space.

Where a multi-modal marker is used within image spaces associated with two separate positioning modalities/systems, the registration equation AX=YB, as referenced above as providing a generic formula for registering one image space to another, the transform 'X' (see FIG. 5), which represents the physical transform between the markers detectable by two separate modalities, may either be set to a known constant or eliminated from the equation as being equal to identity, leaving the equation AX=BY as including only a single unknown variable/transform, 'Y.'

Embodiments of the present disclosure provide markers that present or indicate a reference point in more than one image space (i.e., in image spaces of two separate positioning modalities) by providing a marker that has a co-located center point or other reference point for multiple modalities (e.g., CT/fluoroscopy, and EM). Physically locating the centers of markers for multiple modalities can simplify the transform between detectable markers for multiple modalities. Where such correspondence (transform 'X' in FIG. 5) is known, the 'X' transform can be treated as an identity transform.

Combining markers of multiple modalities in a single marker structure/device to provide a unique known correspondence between such markers can be achieved by implementing a unique size and/or shape for each marker/fiducial. For example, ellipsoids or other shapes having non-symmetrical perspectives providing different view shapes from different view angles can be used to increase the amount of positional information derivable from such markers.

Figure 6:
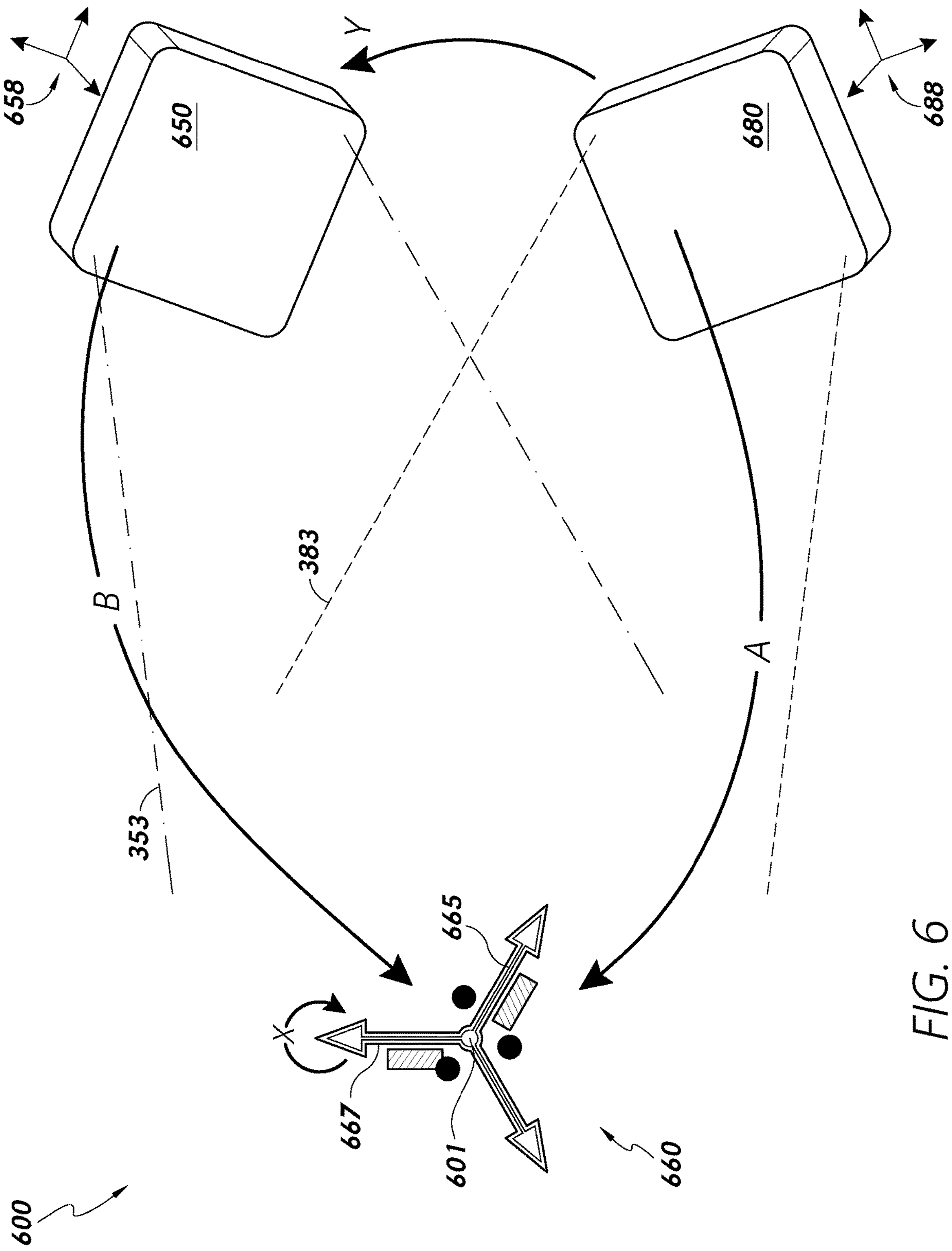
FIG. 6 shows an arrangement of a plurality of positioning systems associated with consolidated markers.

FIG. 6 shows a system 600 including an arrangement of a plurality of positioning systems 650, 680 associated with consolidated markers 665, 667. The system 600 includes a consolidated marker 660 that comprises a mechanical part/component that provides a reference point in more than one modality. For example, the consolidated marker 660 may be visible in image spaces associated with both the first 650 and the second 680 fields/spaces. For example, the first modality 650 may comprise a camera imaging system, a fluoroscopic X-ray imaging system, or a computed tomography (CT) system, whereas the second modality 680 may comprise an electromagnetic field generator positioning system, as described in detail herein. The positioning system 650 may be associated with the coordinate frame 658, whereas the positioning system 680 may be associated with a different coordinate frame 688

In the system 600, the centers 601 of the marker frames 665, 667 are co-localized to provide the common marker/frame 660. Mechanical design of the consolidated marker 660 provides visibility in multiple modalities, wherein such visibility indicates a common center point in the multiple modalities. Although the consolidated marker 660 is shown as having a common center and/or reference frame for both modalities, it should be understood that in some implementations, consolidated markers have center points and orientations that are not identical, but rather offset from one another by a known distance and/or orientation, such that the transform 'X' is a known constant between the two. The markers 665, 667 are combined by some physical linking structure or form, which may cause the coordinate centers of multiple markers to be overlapped in three-dimensional space. For example, the physical 1 inking structure can secure the markers 665, 667 to one another/together in a fixed relationship.

Figure 7:
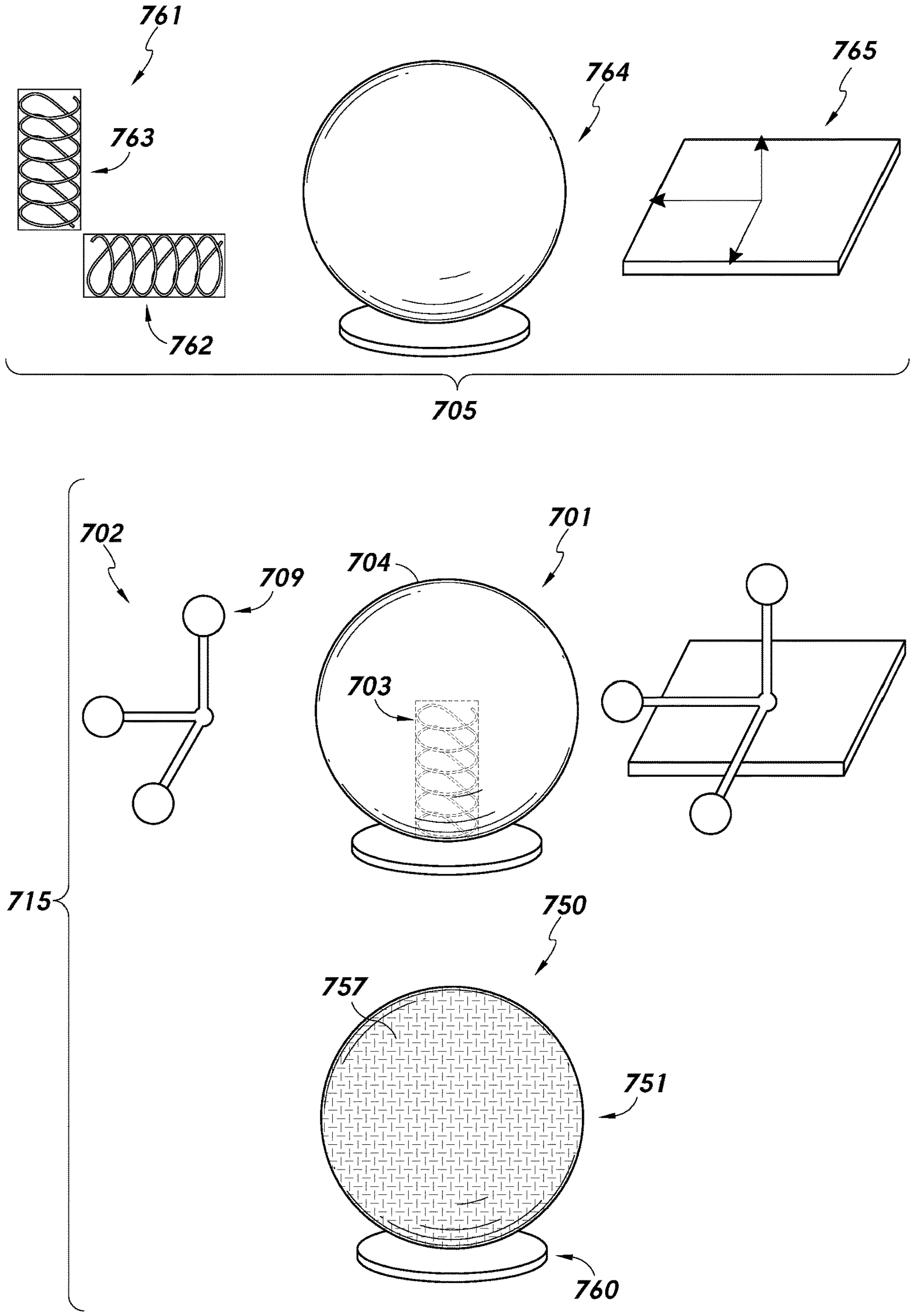
FIG. 7 shows various positioning system markers in accordance with one or more embodiments.

Contemplated herein are consolidated markers combining marker elements visible in any combination of modalities. For example, FIG. 7 shows various combinations of markers 715 in consolidated physical forms. For reference, FIG. 7 further shows example non-consolidated markers 705 that are each visible in a single image space. For example, the marker 761 represents an embodiment of an EM-visible marker including a plurality of conductive coils 762, 763 positioned relative angled orientations with respect one another, wherein such coils can be detectable in an electromagnetic (EM) field produced by an EM field generator system and provide orientation information such that position information derivable therefrom provides more than three or five degrees of freedom. For example, the right-angle orientation of the coils 762, 763 may provide six degrees of freedom in some cases.

The example marker 764 comprises a geometric shape/form (e.g., sphere-shaped bead) that may be visible in a certain imaging modality space. For example, the form/bead 764 may be radiopaque, such that it is visible under a radiation-based imaging modality, such as CT or fluoroscopy (e.g., X-ray), or may be reflective to certain sonic signals, and therefore visible under ultrasonography. Alternatively, the form/bead 764 may be a shape recognizable using a camera-based image processing modality. For example, the bead 764 may reflect infrared (IR) radiation/light in a manner as to allow for positioning thereof. In some embodiments, the center of the geometric form/shape 764 is resolvable in a particular image space.

FIG. 7 further shows another example marker 765, which may be visible in any positioning modality, such as EM positioning, wherein the marker 765 comprises a patch or other fixture that may be placed in the image field for calibration, such as on a patient, surgical table, or other structure. The electromagnetic patch sensor 765 may be arranged in a coordinate frame providing six degrees of freedom. Although described as an electromagnetic patch sensor, the patch sensor 765 may be an optical marker detectable in an optical system image space. Optically-visible markers may be configured such that infrared light/radiation emitted by the relevant emitter of the system reflects off the surface of the marker in a manner as to be detectable with respect to the position of reflection. In some embodiments, the optical imaging source includes stereoscopic cameras.

FIG. 7 further shows various example consolidated markers 715, including a combined EM-visible and CT-, fluoroscopy-, and/or camera-visible geometric form 701 having disposed at or near a center thereof an electromagnetic-visible conductive coil 703. With the added electromagnetic sensor coil 703 integrated within the geometric form 704, the electromagnetic sensor and center of the geometric shape may be co-located. The geometric form 704 may be, for example, a sphere or ellipsoid form. Using different shapes for different markers can serve to allow for such markers to be uniquely identifiable in images (e.g., camera, fluoroscopy, CT, etc.). Furthermore, shape selection for markers can indicate unique matching between EM sensors and the forms/beads they are combined with in the particular embodiment. For example, in a system utilizing multiple EM sensor coils for positioning, each coil may be embedded in or otherwise incorporated with an image-visible form/bead having a different shape, thereby providing additional positional correspondence information. Other examples for uniquely identifying image-visible markers can include using different etchings/patterns on marker surfaces and/or using markers comprising different material properties that allow for unique identification.

With the resolvable centers of the EM sensor 703 and visible form 704 co-located and known, a reference point may be derived in multiple modalities. That is, the center of the marker 701 may be derivable/detectable in both EM space and optical or other imaging space. In some cases, the consolidated markers 715 may be visible in more than two image spaces. For example, the shape of the form 704 may be identifiable in optical space, while the sensor coil 703 may be identifiable in EM space. Additionally or alternatively, the marker 701 may comprise one or more radiopaque markings/surfaces indicating the center of the marker, wherein such markings are identifiable in radiation-based imaging system(s) (e.g., fluoroscopy, CT) and/or sonic imaging system(s) (e.g., ultrasound). The co-location of markers for multiple modalities can simplify registration between such modalities, as described in detail above. Therefore, an identified marker in one space may be trivially converted into a position in another space associated with a separate modality. Therefore, correspondence between two imaging spaces can be determined mechanically and/or instantly, while other solutions may require additional calibration/registration steps.

A combined optical space and EM space marker can be used to identify areas within an EM field volume that that are subject to distortion by comparing EM measurements with optical or other imaging measurements, depending on the type of consolidated marker implemented. That is, optical imaging may be more accurate than EM positioning in some cases due to the potential presence of distortion within the generated electromagnetic field. Such distortion may be caused by, for example, the presence of a fluoroscopy C-arm or other metal structure in the vicinity of the generated field. A consolidated EM and optical marker may be placed within the EM and optical overlapping field volume, wherein the motion of the marker may be tracked in both EM space and optical space to identify areas of deviation between the derived positions in optical space and EM space as indicating electromagnetic distortion. Such distortion, once known, can be accounted for and/or canceled-out in relevant localization computations. In some implementations, the consolidated marker 701 may be constructed by drilling a hole or channel in the geometric form 704 and placing therein the EM sensor 703 in a position such that the center of the geometric form is co-located with the detectable reference of the EM sensor. Co-locating the markers for multiple modalities in accordance with aspects of the present disclosure can obviate the need to construct the coordinate frame transform between the markers for the multiple modalities, thereby simplifying registration of the modalities with one another.

FIG. 7 further shows a consolidated marker 750 including an optical-visible geometric form 751 having a radiopaque surface 757, such that the marker 750 is visible in optical image space as well as radiation-based image space (e.g., fluoroscopy, CT).

As another example, the consolidated marker 702 provides an EM-visible structure defining a coordinate frame, wherein endpoints or other portions of each branch/axis of the coordinate frame include optical-visible (or X-ray-visible) beads/shapes 709, such that the marker 702 can be used for calibration in both EM and optical (or, e.g., X-ray) imaging spaces.

With respect to the registration of two positioning modalities/systems to one another, embodiments of the present disclosure generally are described herein in the context of positioning modalities/systems that provide three-dimensional position information with respect to detected/visible markers. For example, for an optical positioning modality, the camera-based imaging source may include a plurality of cameras at angular offsets relative to one another, such that multiple images from alternate angles are captured from which three-dimensional positional information is derivable. Electromagnetic field generator modalities likewise can determine three-dimensional positional information according to some solutions when a sensor/marker is detected within the electromagnetic field volume. That is, for some modalities, three-dimensional positional information is derivable from a single source position/orientation. However, with respect to some imaging modalities, three-dimensional position information may not be derivable from a single angle. For example, single-camera optical systems and/or X-ray/fluoroscopy systems may be configured to generate only two-dimensional positional information from a given position/orientation of the imaging source (e.g., camera, x-ray emitter).

Figure 8:
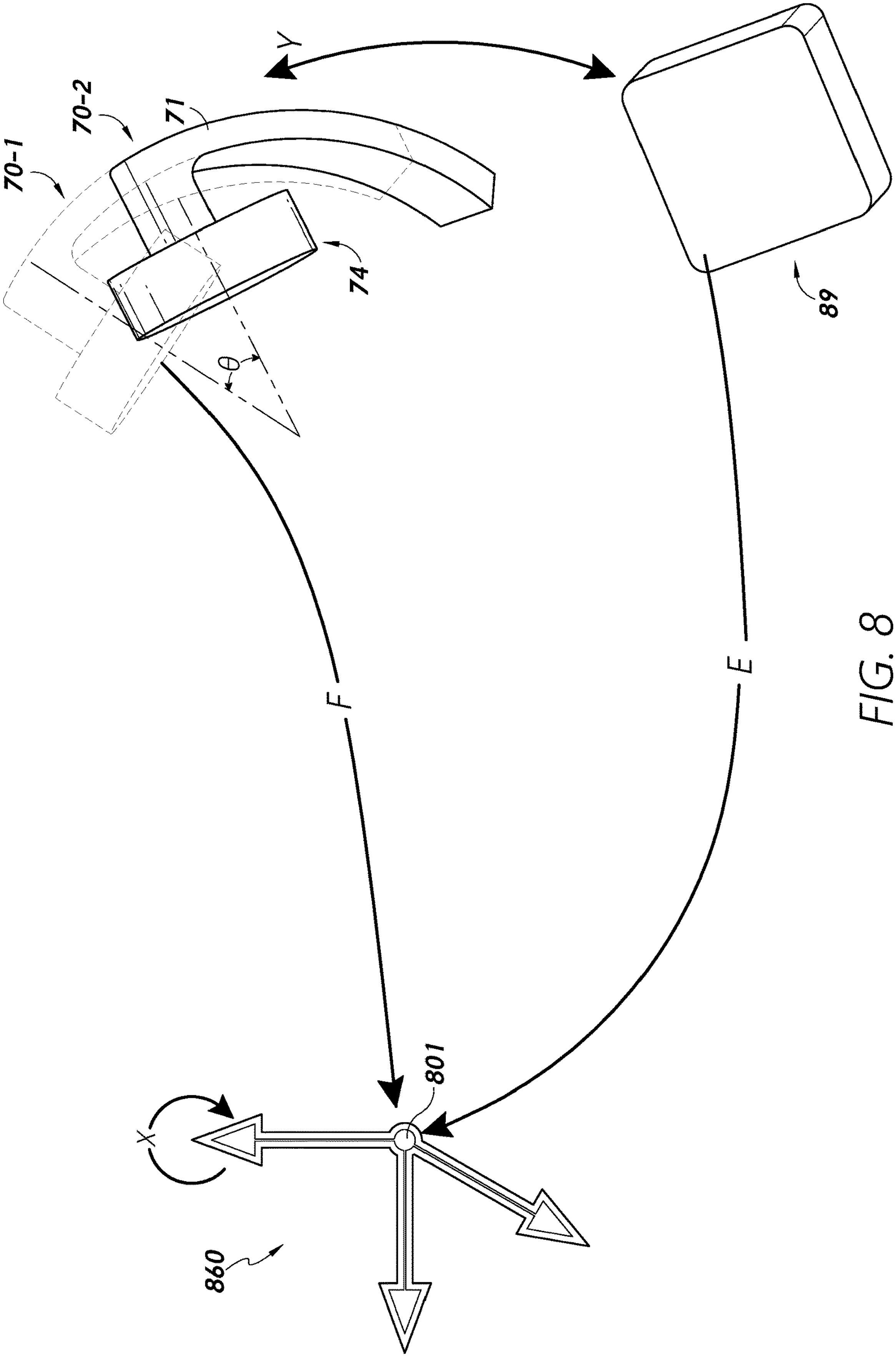
FIG. 8 shows electromagnetic and fluoroscopic positioning systems associated with consolidated marker(s) in accordance with one or more embodiments.

FIG. 8 shows electromagnetic (EM) 89 and fluoroscopic 74 positioning systems associated with consolidated marker(s) 860 in accordance with one or more embodiments, wherein repositioning of the fluoroscopy source 74 may be implemented as a means of generating three-dimensional positional information of the consolidated/co-located marker 860 within the fluoroscopy imaging space. For example, using fluoroscopy, it may be necessary to acquire two or more fluoroscopy/X-ray images to provide sufficient data to triangulate visible markers (e.g., radiopaque fiducials) in three-dimensional space.

FIG. 8 shows a first position 70-1 of the fluoroscopy source 74, wherein imaging of the marker 860 from the first position 70-1 of the source may be implemented to obtain a first image of the detected marker 860 and imaging field of view. Subsequently, the C-arm 71 may be rotated about an axis or otherwise moved to an orientation that is configured to produce an imaging field including the marker 860, wherein the adjusted position 70-2 of the C-arm 71 is oriented at and angular offset θ from the previous position 70-1. Additional image(s) may be generated from the second position 70-2 to provide a plurality of fluoroscopy images of the marker 860 from multiple angles/orientations. The angular separation between the first 70-1 and second 70-2 positions of the fluoroscopy source 74 can be any angular separation. In some implementations, at least 15° (θ) of separation is implemented to provide information from which three-dimensional positional information can be derived. In some implementations, 90° of angular rotation/movement is implemented to provide orthogonal images, which may advantageously provide maximum data for three-dimensional positioning.

With the consolidated marker 860 identifiable with a common or known transform 'X' for two modalities, the transform 'Y' between the positioning systems/sources 74, 89 can be determined based on the three-dimensional position determination 'F' in the fluoroscopy image space, which is based on multiple fluoroscopy images/positions, as well as the three-dimensional position determination 'E' in the EM space, which is based on detection of the marker 860 in the EM field generated from a single position of the EM field generator 89.

Figure 9:
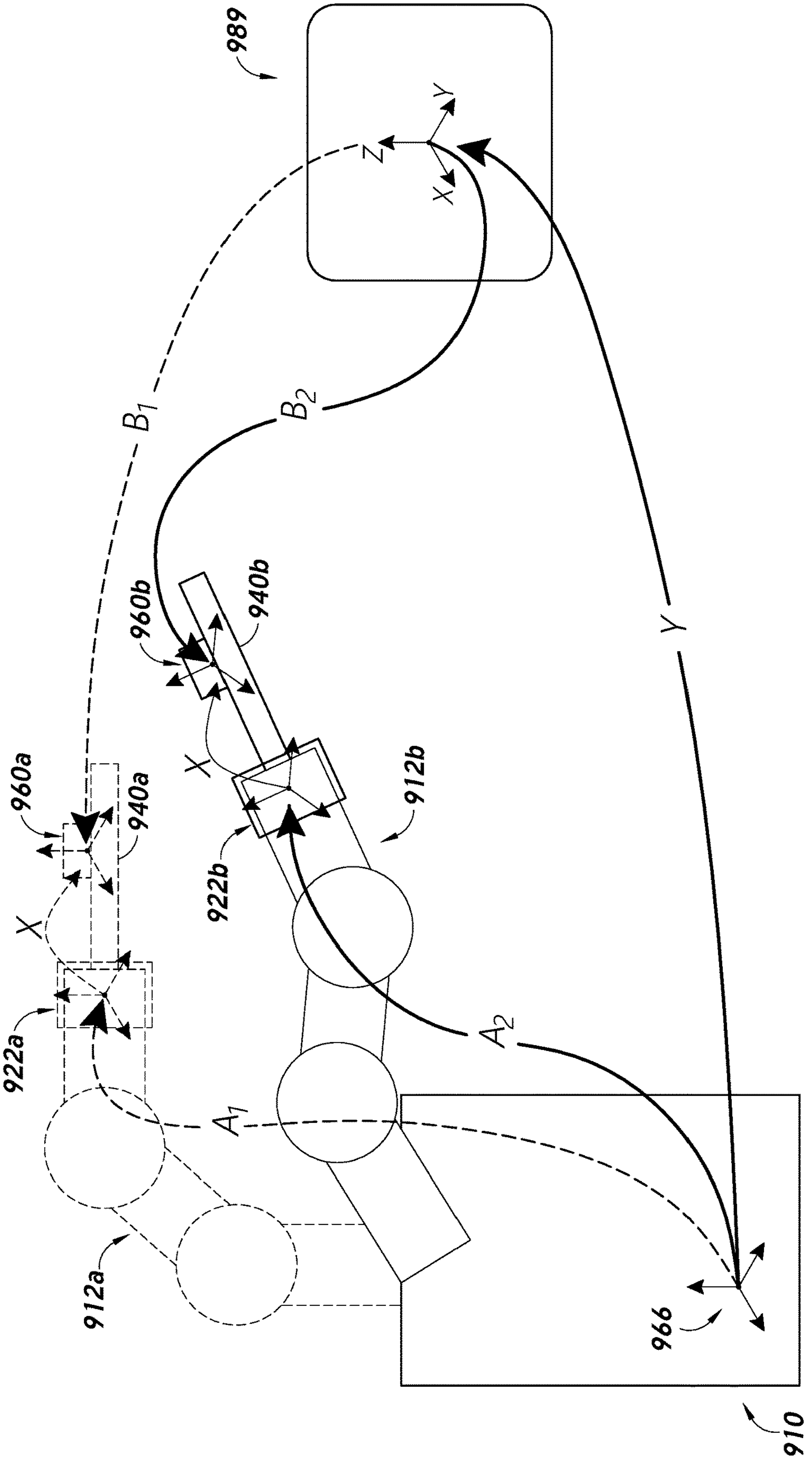
FIG. 9 shows electromagnetic and robotic positioning systems associated with consolidated marker(s) in accordance with one or more embodiments.

FIG. 9 shows electromagnetic (EM) 989 and robotic 910 positioning systems associated with consolidated marker(s) in accordance with one or more embodiments. The robotic system 910 includes a robotic arm 912. FIG. 9 shows two example positions **912*a*, 912*b* of the robotic arm 912** and associated components; the description below can be understood to relate to either position.

The distal end 922 of the robotic arm 912 may comprise an end effector component 922, which may be configured to manipulate certain robotic instrumentation, as described in detail herein. The positioning of the distal end 922 of the robotic arm 912 may be implemented by actuating certain motors or other actuators to cause the various joints and linkages of the robotic arm 912 and/or carriage associated therewith to move and/or articulate to a desired position/ pose. That is, robotic data indicating the present configurations/positions of the various motor/actuator components of the robotic system 910 can indicate the position of the end effector 922 and/or other portion(s) of the robotic arm/system. Therefore, the coordinate frame/space of the robotic system 910 may define a coordinate frame 966, wherein the end effector 922 and/or other portion(s) of the robotic system is positioned relative to, for example, the base of the robotic system.

In order to translate positional information based on robotic data into a coordinate frame space associated with a secondary modality, and/or vice versa, such as EM field generator space or other positioning/imaging modality disclosed herein, registration between the robot space and the secondary modality may be necessary, wherein such registration may be similar conceptually to the registration between imaging/positioning modalities as described above. For example, where the position of the end effector and/or point thereon (and/or other portion(s) of the robotic system) is based on robotic data (represented by the positional transform 'A' in FIG. 9), the "marker" on which the position 'A' is based may be considered the end effector 922 and/or other position indicated by the robotic data. With respect to the marker/fiducial associated with the secondary modality (e.g., EM position sensor), the position vector 'B' may be the position of the relevant EM sensor/marker 960 relative to the field generator 989, as illustrated. That is, the electromagnetic sensor 960 represents the marker visible in the image space of the field generator 989.

In order to simplify the registration process by fixing the physical relationship between the markers/fiducials 922, 960 of the multiple positioning systems/frames, as with other embodiments disclosed herein, a physical link or co-location of the EM sensor 960 with the tracked portion of the robotic arm (e.g., end effector 922) may be implemented so as to set the transform 'X' between the markers of the two systems to a known constant transform and/or identity transform (e.g., co-location of the markers). Therefore, embodiments of the present disclosure may provide for positioning of an EM sensor or other marker associated with an imaging modality on or coupled to a robotic end effector 922 such that the marker 960 is co-located (or in a fixed relationship) with the end effector 922, thereby simplifying the registration between the robot space and the EM image space. For example, the EM sensor 960 may be physically placed on a particular position on or in the end effector or other portion of the robotic arm 912, such that a center thereof is co-located with a position/point trackable using robotic data. Alternatively, a fixture 940 or other rigid structure may couple the sensor 960 to the end effector 922 or other portion of the robotic system, such that a constant fixed positional transform couples the sensor 960 to the robotic marker 922. The fixture 940 may be utilized for marker placement as part of a calibration process.

As described above, registration of two modalities, with reference to FIG. 5, can be based on the relationship AX=YB. The discussion above demonstrates that by producing a fixed physical linkage/relationship between markers associated with multiple positioning modalities, the registration between the modalities can be simplified by obviating the need to calculate the transform 'X.' While embodiments disclosed above are presented in the context of registering separate positioning/imaging modalities involving the detection of markers within a field of view, the disclosed solutions and concepts associated therewith can be implemented in the context of registering a field-of-view positioning/imaging modality to robotic positioning space based on robotic pose data. By mechanically defining the transform between robot space and electromagnetic (EM) field space (or other positioning/imaging space), markers that are detected through field-of-view positioning/imaging (e.g., EM positioning) can be correlated with robotic space without requiring an additional registration step and/or additional workflow steps to determine the transform 'X' between fiducials/markers of the relevant systems.

Fixation of Positioning System Sources

Intrinsic and of an imaging system may be characterized for registration purposes. For example, in order to integrate fluoroscopy imaging in a robotic system, such as the robotic systems in FIGS. 1-3, initially intrinsic calibration of the fluoroscopy system may be implemented, such as by using a reference fixture/probe that is placed in the image space of the fluoroscopy system to calibrate the fluoroscopy system. For example, a checkerboard or other pattern may be printed on the fixture, wherein imaging of the fixture using the fluoroscopy system may be used to compensate for distortion and/or focal length; distortion in the pattern of the reference fixture/structure may indicate distortion in the radiation field. Fluoroscopy image calibration to correct for distortion of artifacts may be implemented to account for pin-cushioning and/or other distortion effects that may be present in some fluoroscopy environments. Taking experimental measurements of the deviation of the relevant electric fields can account for distortion caused by proximity of the metallic C-arm of the fluoroscopy system to the electromagnetic field generator.

With reference back to FIG. 5, registration between multiple positioning systems can be based on the relationship AX=YB, wherein 'X' represents the physical relationship between tracked markers/fiducials of the respective modalities, whereas the transform 'Y' represents the relationship between the sources of the respective image spaces/modalities. Embodiments disclosed above demonstrate how mechanical linkages between the markers/fiducials of multiple modalities can simplify registration between the respective coordinate frames. In a like manner, mechanical linkage between the sources of different modalities, as described herein, can be implemented to simplify multimodality registration. That is, with respect to the paradigm illustrated in FIG. 5 and described in detail herein, the transform 'Y' can be mechanically fixed, thereby setting the transform 'Y' to a constant transform that is known based on the particular mechanical fixation of the imaging sources. When an imaging modality (e.g., camera-based, optical-based, fluoroscopy-based systems) is utilized, fixing the 'Y' transform may be insufficient by itself to transform information or data from a reference frame of another modality to the imaging modality reference frame. For example, it may further be necessary or desirable to implement intrinsic calibration of the imaging modality to get the correct pixel coordinates for implementing transforms between the reference frames.

Figure 10:
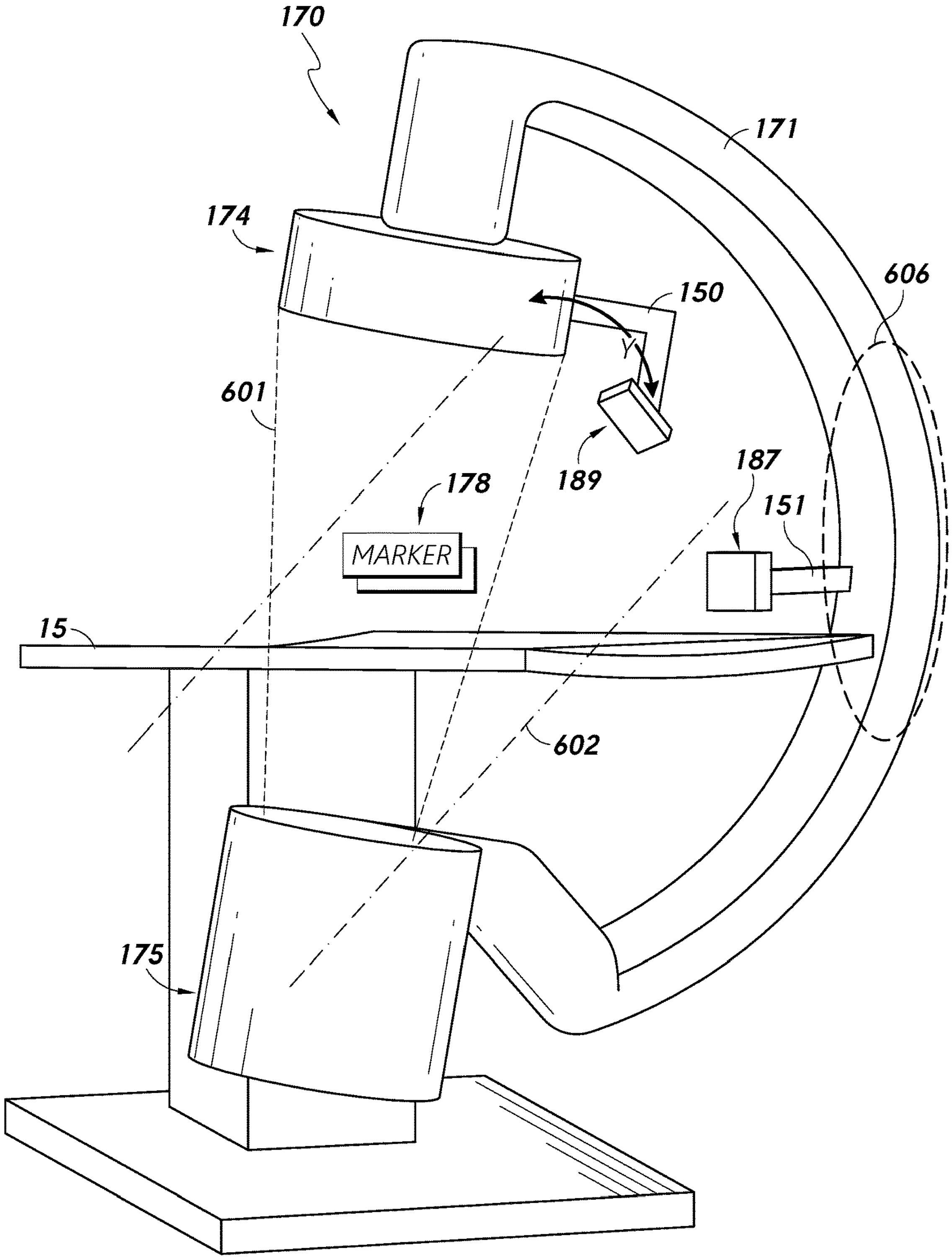
FIG. 10 shows a plurality of positioning systems having sources that are mechanically fixed in accordance with one or more embodiments.

FIG. 10 shows a plurality of positioning systems 170, 189 having sources that are mechanically fixed in accordance with one or more embodiments. Although FIG. 10 shows fixation of an electromagnetic (EM) field generator 189 to a fluoroscopy mounting arm 171 or other structure holding/supporting the source 174 (e.g., metal can structure), it should be understood that the concepts disclosed in connection with FIG. 10 are applicable to the fixation of sources of any type of positioning/imaging modality, and the particular embodiment shown in FIG. 10 is presented for convenience to demonstrate the inventive concepts associated therewith.

With reference back to FIG. 5, a common problem associated with the registering of reference frames of two modalities to one another is the determination of the physical relative position/transform between the position/orientation of the source of the first modality/system and the second modality/system (identified as transform 'Y' in FIG. 5). In the system of FIG. 10, the EM field generator 189 is mechanically fixed via rigid (e.g., non-adjustable/bendable) mounting arm/structure 150 to the fluoroscopy source/receiver 174 and/or C-arm structure 171. Another example fixed mounting to the C-arm structure 171 is shown as field generator 187 mounted to a medial portion 606 of the C-arm 171 via the rigid mounting arm 151.

In the illustrated embodiment, the field generator 189 is rigidly mounted to the structure of the fluoroscopy source/system 170, thereby mechanically defining the physical relationship between the sources 189, 174 of the two imaging systems. C-arms and the fluoroscopic images they are used to create provide a visualization modality that is suitable for inter-operative procedures. EM-based devices/tools can also be used in such settings. Registering these two modalities in a practical manner can be difficult, and embodiments disclosed herein can simplify such registration. Once the fluoroscopic and EM image spaces have been registered, EM-detectable tools/markers 178 can be mapped to fluoroscopic images. Furthermore, once registered, navigation algorithms implemented to direct surgical instrumentation can take advantage of the registration, such as through operator guidance and/or algorithmic processes.

In some embodiments, EM field generators having relatively small form factors may be implemented as a means for practically mounting the EM field generator to the fluoroscopy structure 171. That is, the field generator 189 may comprise a compact field generator, which is smaller in size than example embodiments of the field generator 67 shown in FIG. 1. With a rigid connection between the field generator 189 and the structure 171 of the fluoroscopy system, registration of the EM and fluoroscopy systems can be trivialized.

Establishing a physical relationship between the EM field generator 189 and the fluoroscopy emitter 175 and/or receiver 174 can be achieved by attaching both units/devices to the same support structure (e.g., C-arm 171). With the relationship 'Y' defined between the EM field 602 and fluoroscopy field 601, at least two fluoroscopy images may be generated to provide three-dimensional positional data in the fluoroscopy image space to allow for registration to be completed between the two modalities. EM field position data may be relied upon from a single physical position of the field generator 189, or from two positions associated with the two fluoroscopy images. That is, because the transform between the physical position/orientation of the field generator 189 and the fluoroscopy system 174 is known, when the fluoroscopy system is moved to acquire multiple images for three-dimensional position determination, additional positional information may be utilized for the EM field generator system as well, which may provide additional data points for position determination in the electromagnetic field space.

Physically mounting the field generator 189 to the C-arm 171 can result in distortion of the fluoroscopy field 601 and/or electromagnetic field 602 due to the physical proximity between such sources and/or the proximity to the metal structure 171. In some implementations, calibration may be performed to compensate for determined static distortion resulting from the physical position of the arm 171 on the electromagnetic field 602 to the conductivity and/or other characteristics of the structure 171. In some embodiments, the mounting structure/arm 150 may be of sufficient length to obviate problematic distortion risks from proximity of the components to one another. For example, undesirable radiation may be caused by the structural arm 171 interfering with the EM field 602 of the EM field generator 189 when the structure 171 is disposed within 8 inches or 10 inches of the field generator 189. Therefore, it may be desirable to construct the rigid mounting/coupling arm 150 in a manner as to place the field generator 189 at least such distance away from the fluoroscopy source 174 and/or the structural support arm 171. In such cases, the resulting distortion from interference by the arm 171 may be relatively minimal, such that such distortion can be compensated for by the system control circuitry. Furthermore, in some implementations, the system may be configured to compensate for the distortion profile of the fluoroscopy field 601 with respect to the EM field 602.

In cases in which multi-modal fiducials/markers, as described above, are not utilized, estimation of the transform 'X' between fiducials/markers of fiducials/markers of two positioning systems/modalities can be performed by adjusting the position of the sources of the positioning modalities. For example, positioning data can be generated from a first position of the C-arm 171 and fixed EM field generator 189, 187, after which the C-arm 171 can be positioned at a second position, which may be angled at a different orientation than the first position (e.g., 20° lateral repositioning). Another fluoroscopy image can then be generated while collecting EM data. The difference in the readings/sensing at the two positions relative to the fixed mechanical relationship between the positioning sources, can be used to derive the relative positions of the markers/fiducials. One repositioning, such that two separate fluoroscopy images and associated EM data are collected, can be sufficient for registration. However, it may be desirable to generate fluoroscopy images and associated electromagnetic sensor data at more unique C-arm positions to obtain higher-fidelity registration, although such additional processing may introduce increased workflow time.

The fluoroscopy images may undergo certain processing by the system control circuitry to identify each radiopaque marker and their respective position/orientation in fluoroscopy image space. The relative transform 'X' between the markers/fiducials of the two systems may be resolved from the process data using hand-eye calibration, point-cloud singular value decomposition (SVD), or other process(es). With the field generator 189 mounted to the C-arm 170, the transform between the field generator 189 and the fluoroscopy source 174 is mechanically defined, and therefore the three-dimensional pose of the detected instruments can be overlaid on the fluoroscopy images directly without performing point cloud registration or other registration process.

Although fluoroscopy and EM field positioning modalities are shown in FIG. 10, similar registration concepts may be implemented to register fluoroscopy to an optical vision system, or an optical vision system may be registered to an electromagnetic sensor system. For example, a rigid physical coupling between the EM field generator 189 and a structure associated with an optical camera imaging source may be used to fix the transform 'Y' between such modalities. For some camera systems, it may not be necessary to acquire multiple images from multiple positions/angles in order to derive three-dimensional positional information. For example, stereoscopic camera imaging systems may be configured to determine three-dimensional positional information from a single physical position/orientation of the source device.

Figure 11:
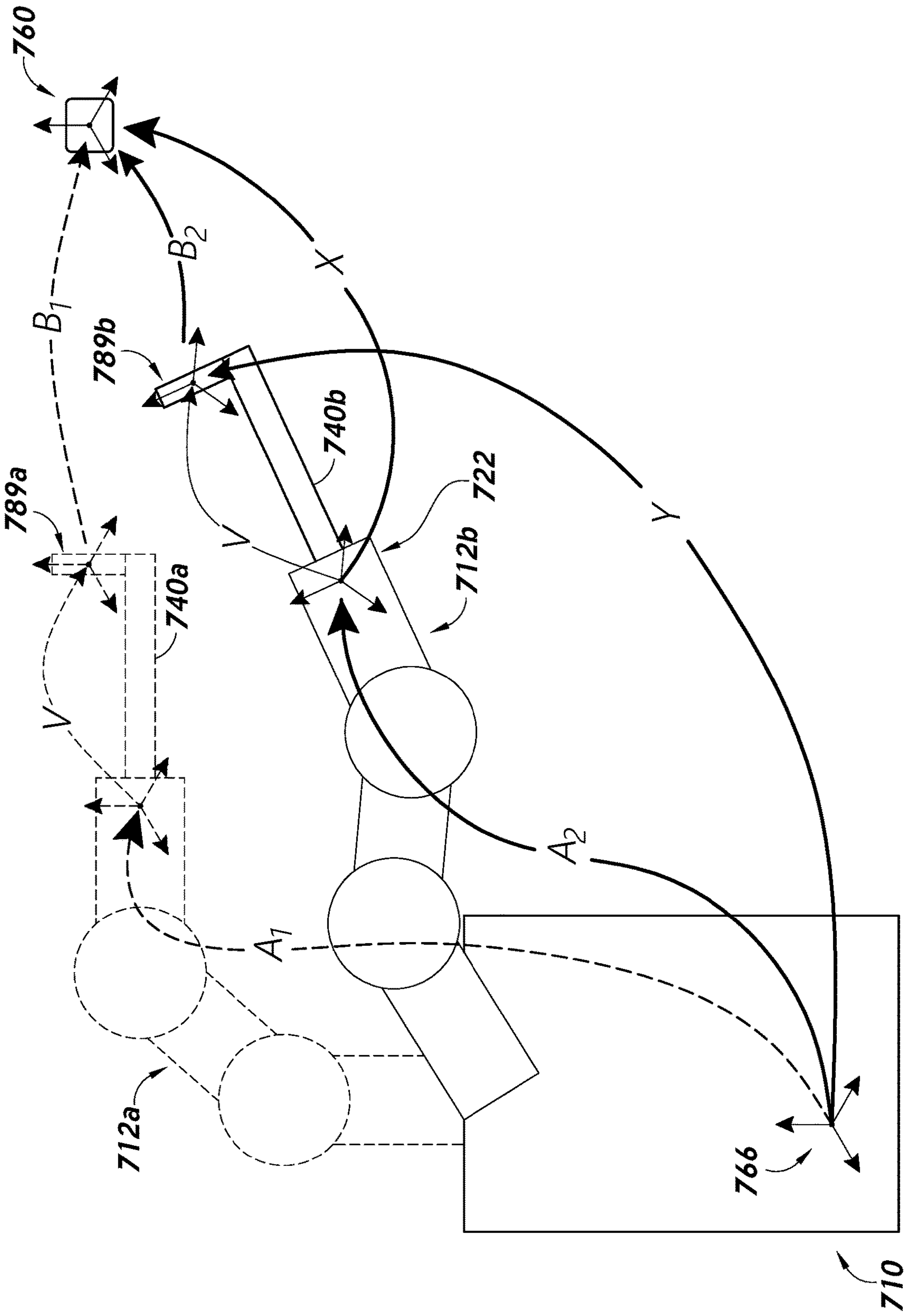
FIG. 11 shows electromagnetic and robotic positioning systems having relatively fixed sources in accordance with one or more embodiments.

FIG. 11 shows electromagnetic (EM) 789 and robotic 710 positioning systems associated with fixed positioning system sources in accordance with one or more embodiments. As described above, registration of two modalities, with reference to FIG. 5, can be based on the equation AX=YB, where: 'B' represents the determined relative position between a first positioning source (e.g., EM field generator) and a marker detected/localized in the reference frame of the first positioning source; 'A' represents the determined relative position between a second positioning system source (e.g., fluoroscopy detector, robotic system base, etc.) and a marker detected/localized in the reference frame of the second positioning source; 'X' represents the physical transform between the marker of the first system and the marker of the second system; and 'Y' represents the physical transform between the source of the first system and the source of the second system.

The discussion above demonstrates that by producing a fixed physical linkage/relationship between positioning system sources associated with multiple positioning modalities, the registration between the modalities can be simplified by obviating the need to calculate the transform 'Y.' While embodiments disclosed above are presented in the context of registering separate positioning/imaging modalities involving the detection of markers within a field of view, the disclosed solutions and concepts associated therewith can be implemented in the context of registering a field-of-view positioning/imaging modality to robotic positioning space based on robotic pose data. By mechanically defining the transform between robot space and electromagnetic (EM) field space (or other positioning/imaging space), markers that are detected through field-of-view positioning/imaging (e.g., EM positioning) can be correlated with robotic space without requiring an additional registration step and/or additional workflow steps to determine the transform 'Y' between sources of the relevant systems.

FIG. 11 shows a robotic system 710 including a robotic arm 712. The distal end 722 of the robotic arm 712 may comprise an end effector component 722, which may be configured to manipulate certain robotic instrumentation, as described in detail herein. The positioning of the distal end 722 of the robotic arm 712 may be implemented by actuating certain motors or other actuators to cause the various joints and linkages of the robotic arm 712 and/or carriage associated therewith to move and/or articulate to a desired position/pose. That is, robotic data indicating the present configurations/positions of the various motor/actuator components of the robotic system 710 can indicate the position of the end effector 722 and/or other portion(s) of the robotic arm/system. Therefore, the imaging space of the robotic system 710 may define a coordinate frame 766, wherein the end effector 722 and/or other portion(s) of the robotic system is positioned relative to, for example, the base of the robotic system. Generally, rather than an absolute position, the identified position of the end effector 722 as determined/controlled based on robotic data may be in a position space that is relative to a physical positioning of the robotic system 710, which may be ambulatory in some instances.

In order to translate positional information based on robotic data into an image space associated with a secondary modality, and/or vice versa, such as EM field generator space or other positioning/imaging modality disclosed herein, registration between the robot space and the secondary modality may be necessary, wherein such registration may be similar conceptually to the registration between imaging/positioning modalities as described above. For example, where the position of the end effector 722 (and/or other portion(s) of the robotic system 710) is based on robotic data (represented by the positional transform 'A' in FIG. 11), the "marker" on which the position 'B' is based may be considered the end effector 722 and/or other portion of the robot arm 712 indicated by the robotic data. With respect to the marker/fiducial associated with the secondary modality (e.g., EM position sensor), the position vector 'B' may be the position of the relevant EM sensor/marker 760 relative to the field generator 789, as illustrated. That is, the electromagnetic sensor 760 represents the marker visible in the image space of the field generator 789.

As referenced, the robot end effector 722 may be considered the relevant fiducial/marker for the robotic system 710, and its position 'A' can be measured using robotic data (e.g., forward kinematics data) with respect to the robot base 710. In order to simplify the registration process by partially fixing the physical relationship between the sources 789, 710 of the multiple positioning systems/frames, as with other embodiments disclosed herein, a physical link between the EM field generator 789 and the robotic system 710 may be implemented to determine the transform 'Y' between the two systems to be equal to a known constant transform relative to the position 'A,' which can be determined according to the robotic data indicating the position of the instrumentation 722 in the robotic space 766. For example, the EM source 789 can be fixed to the robot arm 712, such that the source 789 is fixed at a relative positional transform 'V' relative to the reference point 722 of the robot arm 712. Therefore, the transform 'Y' between the two positioning system sources 789, 710 can be considered equal to the combined vectors 'B' and 'V.' That is, since the illustrated transform 'V' is mechanically defined, 'Y' (i.e., the registration between EM and robot coordinate frames) can be known by fusing robotic (e.g., kinematics) data and the know relationship 'V,' according to the relationship/equation Y=AV; therefore, no separate registration step is needed and EM sensor space can be transformed/translated to robot space directly. It is noted that in the implementation of FIG. 11, the field generator 789 is fixed with respect to the end effector 722 rather than directly to the robot base 710; 'Y' is not determined strictly mechanically, but rather is determined/known based on the mechanical linkage 'V'.

The fixed relationship/transform 'V' may be achieved by mounting the EM field generator 789 to a fixture/tool 740 coupled to the robot arm 712. By implementing the fixed coupling 'V,' embodiments of the present disclosure may provide simplifying of the registration between the robot space and the EM image space. The fixture 740 may be utilized as part of a calibration process for registering the reference frames to one another before or during a surgical procedure.

With the configuration of FIG. 11 implemented, the 'X' transform relationship between the positions of markers/fiducials 760, 722 of the two systems can also be known/determined without additional process steps. For example, with respect to the identified vector transforms in FIG. 11, the transform 'X' may be considered equal to the position 'A' in the EM field space combined with the mechanically-fixed vector 'V.'

As described above, registration of two modalities, with reference to FIG. 5, can be based on the equation AX=YB. The discussion above demonstrates that by producing a fixed physical linkage/relationship between sources associated with multiple positioning modalities, the determining the relationship between markers/fiducials of two modalities have by simplified by obviating the need to calculate the transform 'Y.' As referenced above, the transform 'Y' can be based on the fixed physical transform 'V.' However, creating a precise fixed transform 'V' between the end effector 722 and the EM field generator 789 can be non-trivial and/or difficult to implement in some cases. For example, in the illustrated example of FIG. 11, the transform 'V' is mechanically fixed using a fixture 740 coupled to the end effector 722. However, the process of achieving a precise fixed mechanical relationship 'V' using a fixture or other linking structure can be relatively cumbersome and/or error prone in some cases. For example, where the known physical specifications of the relevant components/assembly are not precisely accurate as attached, the anticipated mechanical definition of the transform 'V' may be off may some amount (e.g., due to manufacturing variances, mechanical slop/clearance, etc.). Therefore, it may be desirable to implement alternative means for simplifying the process of determining the transform 'X' with respect to EM-to-robot space registration.

For example, with further reference to FIG. 11, the unknown transforms 'X' and 'Y' can be estimated in a simplified manner based on movement of the robot arm (i.e., varying 'A') in two or more poses. The first position 712*a* may be understood to represent an initial position, whereas the position 712*b* may be understood to represent a subsequent position after motion of the arm 712.

With respect to the configuration of the system in FIG. 11, pose estimation may be determined for the robotic system 710 based on the change in position $B_\Delta$ of the robot arm reference point and the resulting change in position $A_\Delta$ of the EM sensor 760. For example, the following algorithms may be implemented to perform pose estimation, where calibration/estimation of the pose/position of the EM sensor 760 with respect to the robotic system reference 722 is as follows:

$$A_1 V B_1^{-1} = A_2 V B_2^{-1} \quad (2)$$

$$A_2^{-1} A_1 V B_1^{-1} = V B_2^{-1} \quad (3)$$

$$(A_2^{-1} A_1) V = V (B_2^{-1} B_1) \quad (4)$$

$$A_\Delta V = V B_\Delta \quad (5)$$

$$\mathrm{argmin}_V \sum_{i=1}^{n} \| A_\Delta V - V B_\Delta \| \quad (6)$$

Figure 12:
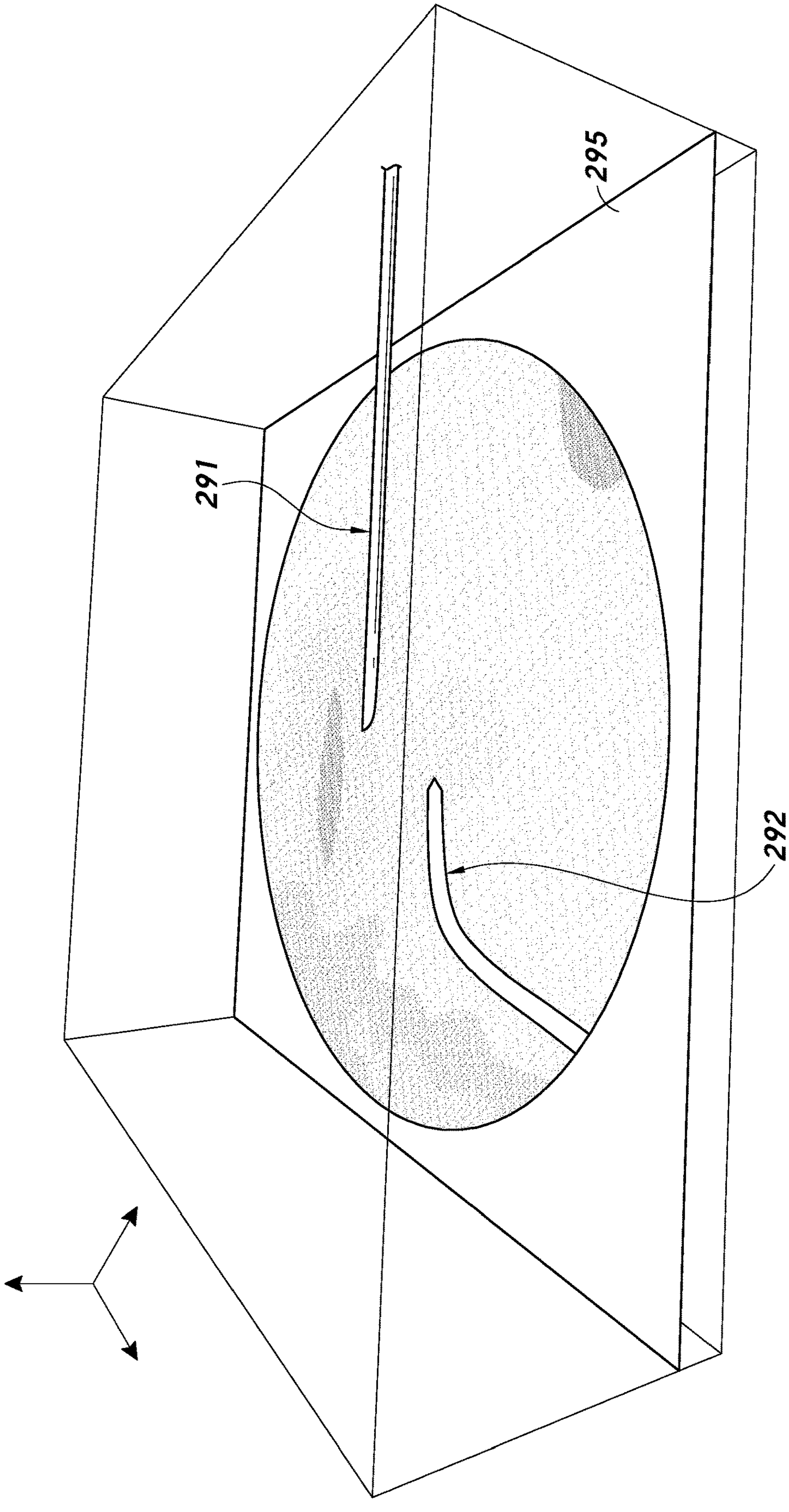
FIG. 12 shows a three-dimensional positional overlay of an instrument representation on a two-dimensional image in accordance with one or more embodiments.

FIG. 12 shows a three-dimensional positional overlay of an instrument representation 291 on a two-dimensional image 295 in accordance with one or more embodiments. FIG. 12 provides an example demonstration of how electromagnetic (EM) sensors can be used to track medical instruments and localize them to a reference image using registration processes that leverage fixed mechanical linkages as described in detail herein. That is, embodiments of the present disclosure advantageously provide a mechanism for projecting object poses known or identified in one image space, such as EM field positioning space, optical space, or the like, onto a two-dimensional fluoroscopy/X-ray space.

FIG. 12 shows a fluoroscopic image 295 that has been generated including certain instrumentation 292 (e.g., scope, needle, etc.) in the image. An overlay process can be performed to overlay the instrument(s) 291 on the captured fluoroscopy image. The system control circuitry can be utilized to localize and display the position of the instrument 291 relative to the patient's anatomy depicted in the image 295.

The tracked instrument 291 can be simulated by rendering it with three-dimensional computer graphics and displaying, overlaying, or superimposing it on the fluoroscopy image 295. The current locations and orientations of the tracking sensors/markers are known relative to the fluoroscopy image space based on the registration with EM space facilitated by mechanical linkage as described herein; the instrument 291 includes one or more EM sensors/markers that allow for registration from EM space to fluoroscopy space. From these known data points, a virtual instrument 921 can be drawn/generated for representation. Robotic data relating to the robotic end effector/system used to control the instrument 291 can also be tracked and this movement can be used to extrapolate the instrument shape between the sensor positions. The rotational orientation of the instrument 291 may also be determined from the sensors as described above to provide an entire three-dimensional reconstruction of the instrument.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., “first” or “second”) may be provided for ease of reference and do not necessarily imply physical characteristics or ordering. Therefore, as used herein, an ordinal term (e.g., “first,” “second,” “third,” etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles (“a” and “an”) may indicate “one or more” rather than “one.” Further, an operation performed “based on” a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms “outer,” “inner,” “upper,” “lower,” “below,” “above,” “vertical,” “horizontal,” and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned “below” or “beneath” another device may be placed “above” another device. Accordingly, the illustrative term “below” may include both the lower and upper positions. The device may also be oriented in the other direction, and thus the spatially relative terms may be interpreted differently depending on the orientations.

Unless otherwise expressly stated, comparative and/or quantitative terms, such as “less,” “more,” “greater,” and the like, are intended to encompass the concepts of equality. For example, “less” can mean not only “less” in the strictest mathematical sense, but also, “less than or equal to.”

What is claimed is:

1. A positioning system comprising:

a group of positioning devices comprising:

a first device comprising a first positioning source associated with a first positioning modality, the first positioning source being configured to view a first field;

a second device comprising a second positioning source associated with a second positioning modality that is of a different type than the first positioning modality, the second positioning source being configured to view a second field;

a third device comprising one or more first markers having a geometric form that is detectable within the first field using the first positioning modality; and a fourth device comprising one or more second markers at least partially embedded within the geometric form of the one or more first markers and detectable within the second field using the second positioning modality, the one or more second markers including one or more conductive coils; and a linking structure physically linking two of the group of positioning devices to one another in a fixed, rigid relative position and orientation.

2. The positioning system of claim 1, wherein the linking structure comprises a rigid mounting arm mounting the second device to the first device.

3. The positioning system of claim 2, wherein:

the first device comprises a movable C-arm; and the first positioning source comprises at least one of an X-ray generator or an X-ray detector.

4. The positioning system of claim 3, wherein the mounting arm mounts the second device to the C-arm of the first device.

5. The positioning system of claim 3, wherein the mounting arm mounts the second device to a structure of the first positioning source.

6. The positioning system of claim 3, wherein the second device comprises an electromagnetic field generator.

7. The positioning system of claim 6, wherein the linking structure mounts the second device to the first device in a manner as to hold the electromagnetic field generator at least eight inches away from the movable C-arm and the first positioning source.

8. The positioning system of claim 1, wherein each of the first and second positioning sources is one of the group consisting of: a camera device, an X-ray emitter, an X-ray detector, an ultrasound emitter, an ultrasound detector, and an electromagnetic field generator.

9. The positioning system of claim 1, wherein the linking structure secures the third device to the fourth device.

10. The positioning system of claim 9, wherein the one or more first markers define a first center position that is co-located with a second center position defined by the one or more second markers.

11. The positioning system of claim 1, wherein the first field is at least partially overlapping with the second field.

12. A positioning marker assembly comprising:

one or more first markers having a geometric form configured to be detected using a first positioning modality;

one or more second markers at least partially embedded within the geometric form of the one or more first markers and configured to be detected using a second modality, the one or more second markers including one or more conductive coils; and a physical linking structure securing the one or more first markers and the one or more second markers in a fixed relative position and orientation.

13. The positioning marker assembly of claim 12, wherein the physical linking structure secures the one or more first markers and the one or more second markers in a co-localized configuration.

14. The positioning marker assembly of claim 13, wherein, in the co-localized configuration, the one or more first markers define a first coordinate center that overlaps a second coordinate center defined by the one or more second markers.

15. The positioning marker assembly of claim 12, wherein:

the one or more first markers comprise one or more radiopaque surfaces.

16. The positioning marker assembly of claim 12, wherein:

the first positioning modality is an optical, ultrasonic, or X-ray imaging modality; and the geometric form comprises a bead form that is visible using the first positioning modality.

17. A positioning system comprising:

a first emitter associated with a first positioning modality, wherein the first emitter is an electromagnetic field emitter;

a second emitter associated with a second positioning modality that is of a different type than the first positioning modality;

one or more first markers having a geometric form that is detectable using the second positioning modality:

one or more second markers at least partially embedded within the geometric form of the one or more first markers and detectable using the first positioning modality;

a C-arm configured to support the second emitter; and a rigid linking arm physically coupling the first emitter to a structure associated with the second emitter so that the first emitter is held away from the C-arm in a fixed, rigid relative position and orientation relative to the second emitter.

18. The positioning system of claim 17, wherein:

the second emitter is an X-ray emitter.

* * * * *